US011905249B2

(12) United States Patent
Ogungbe et al.

(10) Patent No.: US 11,905,249 B2
(45) Date of Patent: Feb. 20, 2024

(54) COVALENT INHIBITORS OF EQUINE ENCEPHALITIS VIRUS

(71) Applicant: Jackson State University, Jackson, MS (US)

(72) Inventors: Ifedayo Victor Ogungbe, Clinton, MS (US); Huaisheng Zhang, Shanghai (CN)

(73) Assignee: Jackson State University, Jackson, MS (US)

( * ) Notice: Subject to any disclaimer, the term of this patent is extended or adjusted under 35 U.S.C. 154(b) by 0 days.

(21) Appl. No.: 17/156,879

(22) Filed: Jan. 25, 2021

(65) Prior Publication Data

US 2022/0235007 A1 Jul. 28, 2022

(51) Int. Cl.
| | |
|---|---|
| *C07D 215/06* | (2006.01) |
| *C07D 215/18* | (2006.01) |
| *C07C 317/28* | (2006.01) |
| *C07D 209/42* | (2006.01) |
| *C07D 241/42* | (2006.01) |
| *C07C 237/36* | (2006.01) |

(52) U.S. Cl.
CPC .......... *C07D 215/06* (2013.01); *C07C 237/36* (2013.01); *C07C 317/28* (2013.01); *C07D 209/42* (2013.01); *C07D 215/18* (2013.01); *C07D 241/42* (2013.01)

(58) Field of Classification Search
CPC .. C07D 215/06; C07D 215/18; C07D 209/42; C07D 241/42; C07C 237/36; C07C 317/28
See application file for complete search history.

(56) References Cited

U.S. PATENT DOCUMENTS

| | | | |
|---|---|---|---|
| 6,287,840 B1 | 9/2001 | Palmer et al. | |
| 7,803,780 B2 | 9/2010 | Kosai et al. | |
| 8,013,014 B2 | 9/2011 | Powers et al. | |
| 8,673,904 B2 | 3/2014 | Bogyo et al. | |
| 9,586,890 B2 * | 3/2017 | Statsyuk | C07D 307/84 |
| 9,982,261 B2 | 5/2018 | Iversen et al. | |
| 10,273,208 B2 * | 4/2019 | Statsyuk | C07D 217/04 |
| 2013/0005759 A1 | 1/2013 | Deiters et al. | |
| 2018/0086749 A1 | 3/2018 | Golden et al. | |
| 2019/0292178 A9 | 9/2019 | Gray et al. | |
| 2020/0096512 A1 | 3/2020 | Herbert et al. | |

FOREIGN PATENT DOCUMENTS

| | | |
|---|---|---|
| WO | 2006091610 A2 | 8/2006 |
| WO | 2007087572 A2 | 8/2007 |

OTHER PUBLICATIONS

Zhang (3), ACS MEd Chem LEtt, (2020), vol. 11, 2139-2145. (Year: 2020).*
Zhang (2), Bioorg & MEd Chem LEtt, vol. 30, (2020), 127217, 1-6. (Year: 2020).*
Zhang(1), Bioorg & MEd Chem Lett, vol. 28, (2018), 1647-1651. (Year: 2018).*
Kathman, J AmChem Soc, vol. 137 (2015), 12442-12445. (Year: 2015).*
Aguilar, P.V.; Estrada-Franco, J.G.; Navarro-Lopez, R.; Ferro, C.; Haddow, A.D.; Weaver, S.C. Endemic Venezuelan equine encephalitis in the Americas: hidden under the dengue umbrella. Future Vi-rol. 2011, 6, 721-740.
Sharma, A; Knollmann-Ritschel, B. Current Understanding of the Molecular Basis of Venezuelan Equine Encephalitis Virus Pathogenesis and Vaccine Development. Viruses 2019, 11, 164.
Carrera, J.P; Bagamian, K.H.; Travassos da Rosa, A.P.; Wang, E.; Beltran, D.; Gundaker, N.D.; Armien, B.; Arroyo, G.; Sosa, N.; Pascale, J.M.; Valderrama, A.; Tesh, R.B.; Vittor, A.Y.; Weaver, S.C. Human and Equine Infection with Alphaviruses and Flaviviruses in Panamá during 2010: A Cross-Sectional Study of Household Contacts during an Encephalitis Outbreak. Am J Trop Med Hyg 2018, 98, 1798-1804.
Zacks, M.A.; Paessler, S. Encephalitic alphaviruses. Vet Microbiol, 2011, 140, 281-286.
Morens, D.M., Folkers, G.K.; Fauci, A. S. Eastern Equine Encephalitis Virus—Another Emergent Arbovirus in the United States, N Engl J Med, 2019, 381:1989-1992.
Kosasih H.; de Mast, Q.; Widjaja, S.; Sudjana, P.; Antonjaya, U.; Ma'roef, C.; Riswari, S.F.; Porter, K.R.; Burgess, T.H.; Alisjahbana, B., et al. Evidence for Endemic Chikungunya Virus Infections in Bandung, Indonesia. PLOS Negl. Trop. Dis. 2013, 7, e2483.
Kim, D. Y.; Atasheva, S.; Frolova, E. I.; Frolov, I. Venezuelan eq-uine encephalitis virus nsP2 protein regulates packaging of the viral genome into infectious virions. Journal of virology 2013, 87, 4202-4213.
Campos-Gomez, J.; Ahmad, F.; Rodriguez, E.; Saeed, M.F. A novel cell-based assay to measure activity of Venezuelan equine encephalitis virus nsP2 protease. Virology 2016, 496, 77-89.
Hu, X.; Compton, J.R.; Leary, D.H.; Olson, M.A.; Lee, M.S.; Cheung, J.; Ye, W.; Ferrer, M.; Southall, N.; Jadhav, A.; Morazzani, E.M. Glass, P.J; Marugan, J. and Legler, P.M. Kinetic, Mutational, and Structural Studies of the Venezuelan Equine Encephalitis Virus Nonstructural Protein 2 Cysteine Protease. Biochemistry 2016, 55, 3007-3019.
Skidmore, A.M.; Adcock, R.S.; Jonsson, C.B.; Golden, J.E.; Chung, D.H. Benzamidine ML336 inhibits plus and minus strand RNA syn-thesis of Venezuelan equine encephalitis virus without affecting host RNA production. Antiviral Research 2020, 174, 104674.
Jonsson, C.B.; Cao, X.; Lee, J.; Gabbard, J.D.; Chu, Y.K.; Fitzpatrick, E.A.; Julander, J.; Chung, D.H.; Stabenow, J.; Golden, J.E. Efficacy of a ML336 derivative against Venezuelan and eastern equine encephalitis viruses. Antiviral research 2019, 167, pp. 25-34.

(Continued)

*Primary Examiner* — D Margaret M Seaman
(74) *Attorney, Agent, or Firm* — Butler Snow LLP

(57) ABSTRACT

Embodiments and methods for a new class of potent non-peptidic covalent inhibitors of nsP2 cysteine protease that inhibit Venezuelan equine encephalitis virus's (VEEV) replication in neuroblasts are disclosed. More particularly, an acrylate and vinyl sulfone-based chemical series were investigated as promising starting scaffolds against VEEV and as inhibitors of the cysteine protease domain of VEEV's nonstructural protein 2 (nsP2). The invention discloses compounds of Formula I and analogues for treatment of VEEV.

18 Claims, 10 Drawing Sheets

(56) References Cited

OTHER PUBLICATIONS

Mcshan, D.; Kathman, S.; Lowe, B.; Xu, Z.; Zhan, J.; Statsyuk, A.; Ogungbe, I.V. Identification of non-peptidic cysteine reactive fragments as inhibitors of cysteine protease rhodesain. Bioorganic & medicinal chemistry letters 2015, 25, 4509-4512.

Kathman, S.G.; Xu, Z.; Statsyuk, A.V. A fragment-based method to discover irreversible covalent inhibitors of cysteine proteases. J Med Chem 2014, 57, 4969-4974.

Rico-Hesse, R.; Weaver, S.C.; De Siger, J.; Medina, G.; Salas, R.A. Emergence of a new epidemic/epizootic Venezuelan equine encephalitis virus in South America. Proceedings of the National Academy of Sciences 1995, 92, 5278-5281.

Improved AZA-peptide Epoxides. Retrieved from https://licensing.research.gatech.edu/technology/improved-aza-peptide-epoxides.

Multivalent Virus Like Particle Vaccine Against Arboviruses. Retrieved from https://www.depts.ttu.edu/research/commercialization/industry/index.php/technologies/d-1584_multivalent-virus-like-particle-vaccine-against-arbovirus.

Method for the Generation, Expansion, and Maintenance of Type-1 Regulatory T Cells. Retrieved from https://cornell.flintbox.com/technologies/dac93556-ee21-4e2a-a544-82d4f9f34e9e.

Huang, W., Solouki, S., Koylass, N. et al. ITK signalling via the Ras/IRF4 pathway regulates the development and function of Tr1 cells. Nat Commun 8, 15871 (2017). https://doi.org/10.1038/ncomms15871.

Taylor, K.G. and Paessler, S., 2013. Pathogenesis of Venezuelan equine encephalitis. Veterinary microbiology, 167 (1-2), pp. 145-150.

Lee GM, Balouch E, Goetz DH, Lazic A, Mckerrow JH, Craik CS. Mapping inhibitor binding modes on an active cysteine protease via nuclear magnetic resonance spectroscopy. Biochemistry. Dec. 18, 2012;51(50): 10087-98. doi: 10.1021/bi301305k. Epub Dec. 10, 2012. PMID: 23181936; PMCID: PMC3566641.

Bates JT, Pickens JA, Schuster JE, Johnson M, Tollefson SJ, Williams JV, Davis NL, Johnston RE, Schultz-Darken N, Slaughter JC, Smith-House F, Crowe JE Jr. Immunogenicity and efficacy of alphavirus-derived replicon vaccines for respiratory syncytial virus and human metapneumovirus in nonhuman primates. Vaccine. Feb. 10, 2016;34(7):950-6. doi: 10.1016/j.vaccine.2015.12.045. Epub Jan. 7, 2016. PMID: 26772634; PMCID: PMC4731299.

Wagner B, Hillegas JM, Babasyan S. Monoclonal antibodies to equine CD23 identify the low-affinity receptor for IgE on subpopulations of IgM+ and IgG1+ B-cells in horses. Veterinary Immunology and Immunopathology 146 (2012) 125-134.

Hanssen IM, Lapidot M, Thommas BPHJ. Emerging Viral Disease of Tomato Crops. MPMI vol. 23, No. 5, 2010, pp. 539-548. doi: 10.1094/MPMI -23-5-0539.

Reichert, E.; Clase, A.; Bacetty, A.; Larsen, J. Alphavirus antiviral drug development: scientific gap analysis and prospective research areas. Biosecurity and bioterrorism: biodefense strategy, practice, and science 2009, 7, 413-427.

Lemant, J.; Boisson, V.; Winer, A., Thibault, L.; André, H.; Tixier, F.; Lemercier, M.; Antok, E.; Cresta, M.P.; Grivard, P., et al. Serious acute chikungunya virus infection requiring intensive care during the reunion island outbreak in 2005-2006. Crit. Care Med., 2008, 36, 2536-41.

Angelini, P.; Macini, P.; Finarelli, A.C.; Pol, C.; Venturelli, C.; Bellini, R.; Dottori, M. Chikungunya epidemic outbreak in Emilia-Romagna (Italy) during summer 2007. Parasitologia 2008, 50, 97-98.

Berge, T.O.; Banks, I.S.; Tigertt, W.D. Attenuation of Venezuelan Equine Encephalomyelitis Virus by ire vitro Cultivation in Guinea-Pig Heart Cells. American Journal of Hygiene 1961, 73, 209-218.

Compton JR, Mickey MJ, Hu X, Marugan JJ, Legler PM. Mutation of Asn-475 in the Venezuelan Equine Encephalitis Virus nsP2 Cysteine Protease Leads to a Self-Inhibited State. Biochemistry. Nov. 28, 2017;56(47):6221-6230. doi: 10.1021/acs.biochem.7b00746. Epub Nov. 9, 2017. PMID: 29064679.

Sbaraglini ML, Bellera CL, Fraccaroli L, Larocca L, Carrillo C, Talevi A, Alba Soto CD. Novel cruzipain inhibitors for the chemotherapy of chronic Chagas disease. Int J Antimicrob Agents. Jul. 2016;48(1):91-95. doi: 10.1016/j.ijantimicag.2016.02.018. Epub Apr. 22, 2016. PMID: 27216381.

McAleese SM, Brown JK, Macrae Al, Mackellar A, Huntley JF, Miller HR. Cloning and expression of the extra-cellular part of the alpha chain of the equine high-affinity IgE receptor and its use in the detection of IgE. Vet Immunol Immunopathol. Mar. 15, 2006;110(1-2):187-91. doi: 10.1016/j.vetimm.2005.09.006. Epub Oct. 7, 2005. PMID: 16216338.

Pyo HM, Masic A, Woldeab N, Embury-Hyatt C, Lin L, Shin YK, Song JY, Babiuk S, Zhou Y. Pandemic H1N1 influenza virus-like particles are immunogenic and provide protective immunity to pigs. Vaccine. Feb. 8, 2012;30(7):1297-304. doi: 10.1016/j.vaccine.2011.12.083. Epub Dec. 27, 2011. PMID: 22207090.

Sabban, Sari; Ye, Hongtu; Helm, Birgit. Development of an in vitro model system for studying the interaction of Equus caballus IgE with its high-affinity receptor FcaRI. Veterinary immunology and immunopathology. 2013 153. Doi:10.1016/j.vetimm.2013.01.008.

* cited by examiner

| Entry | R | 1-4 HeLa (VEEV IC-SH3) EC₅₀(μM) | CC₅₀(μM) | SI | 5-8 VeroE6 (VEEV IC-SH3) EC₅₀(μM) | CC₅₀(μM) | SI |
|---|---|---|---|---|---|---|---|
| 1 | (HN-substituted structure) | 0.55 ± 0.10<br>4.45 ± 3.53$^a$ | >30.00<br>6.71$^a$ | >54.50<br>1.51$^a$ | 6.48 ± 1.94<br>>25.00$^a$ | >30.00<br>18.10$^a$ | >4.63<br>- |
| 2 | (HN-substituted structure) | 1.15 ± 0.08<br>>25.00$^a$ | >30.00<br>11.43$^a$ | >26.10<br>- | 8.19 ± 3.08<br>22.33 ± 10.62$^a$ | >30.00<br>>25.00$^a$ | >3.67<br>>1.12$^a$ |
| 3 | (HN-substituted structure) | 8.63 ± 0.75 | >30.00 | >3.50 | 8.63 ± 2.49 | >30.00 | >3.48 |
| 4 | (HN-substituted structure) | 18.24 ± 1.38 | >30.00 | >1.70 | >30.00 | >30.00 | - |
| 5 | (HN-substituted structure) | >30.00 | >30.00 | - | >30.00 | >30.00 | - |
| 6 | (HN-substituted structure) | >30.00 | >30.00 | - | >30.00 | >30.00 | - |
| 7 | (HN-substituted structure) | >30.00 | >30.00 | - | >30.00 | >30.00 | - |
| 8 | (HN-substituted structure) | >30.00 | >30.00 | - | >30.00 | >30.00 | - |

FIG. 2A

| Entry | R | Human BE(2)-M17 (TC83) | | | Mouse Neuro-2a (TC83) | | |
|---|---|---|---|---|---|---|---|
| | | EC50(μM) | CC50(μM) | SI | EC50(μM) | CC50(μM) | SI |
| 9 | (indole-Br) | 3.23 ± 4.84 | 12.04 | 3.72 | 11.13 ± 4.51 | >25.00 | >2.24 |
| 10 | (HN) | 2.24 ± 1.28 | 19.62 | 8.77 | 5.05 ± 1.82 | 27.36 | >4.95 |
| | | 3.86 ± 0.95[a] | 6.68[a] | 1.73[a] | 3.95 ± 1.17[a] | 9.61[a] | 1.88[a] |
| 11 | (HN) | 1.35 ± 0.74 | >25.00 | >18.46 | 2.33 ± 1.02 | >25.00 | >11.74 |
| | | 1.62 ± 0.28[a] | 17.36[a] | 10.74[a] | 4.38 ± 4.86[a] | 19.18[a] | 4.37[a] |
| 12 | (HN) | 4.49 ± 0.21 | >25.00 | >5.56 | 3.43 ± 0.09 | >25.00 | >7.28 |
| 13 | (HN) | 3.33 ± 0.24 | >25.00 | >7.50 | 3.70 ± 0.24 | >25.00 | >6.71 |
| 14 | (HN) | 17.28 ± 8.78 | >37.92 | >2.19 | 13.22 ± 5.83 | >5000 | >4.16 |
| 15 | (HN) | 9.34 ± 2.79 | >5000 | >5.3 | 13.21 ± 8.78 | >5000 | >3.79 |
| 16 | (N) | 17.09 ± 5.02 | 16.47 | 0.96 | 19.12 ± 15.35 | 46.34 | 2.08 |
| ML336 | Ref. 13 | 0.01 ± 0.00 | >2.50 | >250.00 | 0.02 ± 0.01 | >2.50 | >125.00 |

COVALENT INHIBITORS OF EQUINE ENCEPHALITIS VIRUS

FEDERALLY SPONSORED RESEARCH

This invention was made with government support under grant SC3GM122629 awarded by the National Institutes of Health. The government has certain rights in the invention.

FIELD OF THE INVENTION

The present invention is generally directed towards covalent inhibitors for treatment of encephalitis virus. More particularly, it is directed towards a method for using covalent inhibitors to block the replication of equine encephalitis virus.

BACKGROUND OF THE INVENTION

Venezuelan equine encephalitis virus (VEEV) is a mosquito-borne neurotropic virus. VEEV infections can induce flu-like symptoms and can progress to encephalitis and death. Fourteen antigenic subtypes of VEEV have been identified to date. Symptomatic diseases caused by antigenic subtypes IA/B, IC, and IE in equines and humans have been reported while subtype ID is typically avirulent in equines but virulent in humans. New World alphaviruses like VEEV, eastern equine encephalitis virus (EEEV), and western equine encephalitis virus (WEEV) are widely distributed in North, Central and South America. Occasional outbreaks of VEEV have been reported over the years in the Americas. The use of VEEV as a bioweapon was evaluated by both the US and Russia during the Cold War. New World alphaviral infection f3' UTR has a poly(A) tail. One of the two open reading frames in its genome encodes the non-structural polyprotein precursor nsP1, nsP2, nsP3, nsP4. Its final products, viral non-structural proteins (nsP1, nsP2, nsP3 and nsP4), are obtained via proteolytic hydrolysis of the polyprotein precursor by virus-encoded cysteine protease (nsP2). Replication of the viral genome as well as the transcription of its 26S sub-genomic viral RNA relies on the biochemical actions of nsP1, nsP2, nsP3 and nsP4. The viral structural proteins, capsid protein (CP), small peptides (E3 and 6K), and the envelope glycoproteins (E1 and E2) are translated from the 26S sub-genomic viral RNA. VEEV nsP2 is an important drug target due to the crucial roles it plays in the virus. Apart from proteolytic hydrolysis of the non-structural polypeptide precursor into functional protein units, nsP2 regulates negative strand RNA synthesis via its methyltransferase activity. In addition, nsP2 facilitates the packaging of genomic RNA into virus particles.

To date, only a few compounds have been reported to inhibit both the protease activity of VEEV's nsp2 and the replication of VEEV.

Virology 2016, 496, 77-89 discloses few compounds including CA-074Me and E64-d to be inhibiting both the protease activity of VEEV's nsp2 and the replication of VEEV, albeit marginally.

Antiviral research 2019, 167, pp. 25-34 and Antiviral Research 2020, 174, 104674 disclose a series of benzamidine-based and potent inhibitors of VEEV, that inhibits viral RNA synthesis, that is currently under pre-clinical investigation.

WO2006091610A2 discloses a papain like inhibitor of cysteine protease. The papain-like cysteine protease inhibitor is a cathepsin inhibitor. The cathepsin inhibitor is effective against the infection caused by enveloped virus.

US20180086749A1 discloses heterocyclic compound for the treatment of Chikungunya virus, Zika virus, Venezuelan equine encephalitis virus, and/or respiratory syncytial virus infection.

U.S. Pat. No. 8,673,904B2 discloses epoxide inhibitors of cysteine proteases, compositions comprising the epoxide inhibitors, and packaged pharmaceuticals. These claimed structures do not mention the use of these compounds for inhibiting protease activity of VEEV's nsp2 and the replication of VEEV.

U.S. Pat. No. 6,287,840B1 discloses irreversible cysteine protease inhibitors based upon an alkene bond being conjugated to an electron withdrawing group. The inhibitor structure also provides a targeting peptide which is specific for different cysteine proteases.

Therefore, there remains an unmet need of compound(s) that can be effectively used in treatment of encephalitis viruses by inhibiting both the protease activity of VEEV's nsp2 and the replication of VEEV.

SUMMARY OF THE INVENTION

It is the aim of the invention to provide a new class of potent non-peptidic covalent inhibitors of nsP2 cysteine protease that inhibit Venezuelan equine encephalitis virus's (VEEV) replication in neuroblasts. The structures claimed herein the present invention are non-peptidic covalent inhibitors of nsP2 cysteine protease inhibiting alphaviral replication, more particularly VEEV's replication.

An embodiment of the present invention provides methods to investigate acrylate and vinyl sulfone-based chemical series of compounds as promising starting scaffolds against VEEV and as inhibitors of the cysteine protease domain of VEEV's non-structural protein 2 (nsP2). The method comprises performing primary screening and dose response studies to evaluate the potency and cytotoxicity of the compounds. The results provide structural insights into a new class of potent non-peptidic covalent inhibitors of nsP2 cysteine protease that can also inhibit VEEV's replication in neuroblasts.

It is still further an aim of the invention to facilitate the evolution of the vinyl sulfone-based chemical series of compounds into selective and broad-spectrum anti-alphaviral drug leads.

Embodiments of the invention provide compound(s) of Formula (I)

Formula I a stereoisomer, solvate and/or pharmaceutical acceptable salt thereof; wherein A is $C(O)OR_3$ or $S(O_2)R_3$;

$R_3$ is (C1-6)alkyl, (C3-7) cycloalkyl, (C3-7) cycloalkyl(C1-5)alkyl, optionally substituted aryl, or optionally substituted (C6-12)aralkyl;

$R_1$ and $R_2$ are independently selected from H, (C1-6)alkyl, (C3-7)cycloalkyl, (C3-7)cycloalkyl(C1-5)alkyl, optionally substituted aryl, or optionally substituted (C6-12) aralkyl;

R is a group selected from

---- is a single bond or a double bond.

Specifically, the present invention provides compound of Formula II:

Formula II or a stereoisomer, solvate and/or pharmaceutical acceptable salt thereof;
wherein A, $R_1$, $R_2$, $R_3$ and R are as above,
more specifically in another embodiment $R_1$ is H, methyl or benzyl and $R_2$ is H or methyl.

In yet another embodiment, the compound of formula (I) is disclosed wherein substituents on optionally substituted aryl or optionally substituted (C6-12)aralkyl in $R_3$, $R_1$ and $R_2$ are selected from (C1-6)alkyl, (C1-6)alkoxy, halogen, halogen substituted (C1-6)alkyl, hydroxyl or amino.

In an embodiment, the invention provides a composition comprising compound of formula (I) as inhibitors of the cysteine protease domain of Venezuelan equine encephalitis virus (VEEV's) non-structural protein 2 (nsp2).

Further the invention provides a method of treating infectious disease caused by Venezuelan equine encephalitis virus (VEEV) comprising administering a compound of Formula (I) to the patient.

The present invention provides a compound of Formula (III)

Formula III or a stereoisomer, solvate and/or pharmaceutical acceptable salt thereof; wherein
$R_4$ is (C1-6)alkyl, (C3-7)cycloalkyl, (C3-7)cycloalkyl(C1-5)alkyl, optionally substituted aryl, or optionally substituted (C6-12)aralkyl;
$R_5$ and $R_6$ are independently selected from H, (C1-6)alkyl, (C3-7)cycloalkyl, (C3-7)cycloalkyl(C1-5)alkyl, optionally substituted aryl, or optionally substituted (C6-12) aralkyl;
$R_7$ is a group selected from wherein R$_5$ is H,
wherein R$_5$ is CH$_3$,
wherein R$_5$ is benzyl,
wherein R$_6$ is H,
wherein R$_6$ is CH$_3$.

In an embodiment, the compound of formula (III) are provided wherein substituents on optionally substituted aryl or optionally substituted (C6-12)aralkyl in R$_4$, R$_5$ and R$_6$ are selected from (C1-6)alkyl, (C1-6)alkoxy, halogen, halogen substituted (C1-6)alkyl, hydroxyl or amino More particularly the present invention provides the compounds The invention additionally provide composition comprising compound(s) of formula (III) as inhibitors of the cysteine protease domain of Venezuelan equine encephalitis virus (VEEV's) non-structural protein 2 (nsp2).

Embodiments of the invention provide method of treating infectious disease caused by Venezuelan equine encephalitis virus (VEEV) comprising administering a compound of Formula (III) to the patient.

BRIEF DESCRIPTION OF FIGURES

Further advantages of the invention will become apparent by reference to the detailed description of preferred embodiments when considered in conjunction with the drawings, which are not to scale, wherein like reference characters designate like or similar elements to the several drawings as follows:

FIG. 2A shows the details of the Anti-VEEV activity of compounds 1-8.

DETAILED DESCRIPTION

Figure 1A:
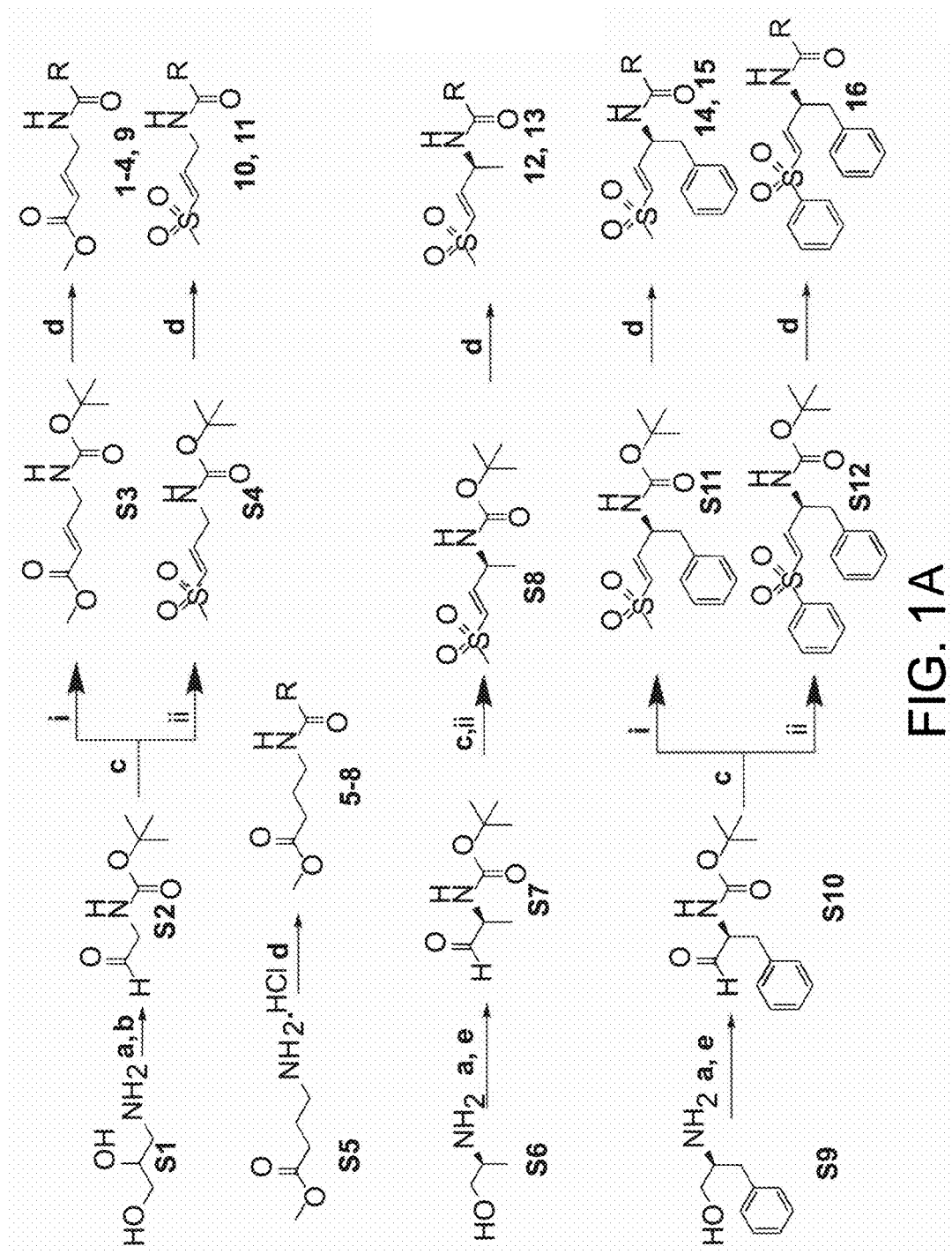
FIGS. 1A, 1B and 1C depict synthesis of target compounds—Scheme 1—compounds 1-16 and Scheme S1—compounds 1-43 respectively.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one with high skilled in the art, and the general principles defined herein may be applied to other embodiments and applications without departing from the scope of the invention. The present invention is not intended to be limited to the embodiments shown but is to be accorded the widest possible scope consistent with the principles and features disclosed herein.

Emerging infectious diseases like those caused by arboviruses such as VEEV pose a serious threat to public health systems. Development of medical countermeasures against emerging infectious diseases are of utmost importance. An acrylate and vinyl sulfone-based chemical series was investigated as promising starting scaffolds against VEEV and as inhibitors of the cysteine protease domain of VEEV's nonstructural protein 2 (nsP2). The investigation provided structural insights into a new class of potent non-peptidic covalent inhibitors of nsP2 cysteine protease that can also inhibit VEEV's replication in neuroblasts. Thus, the method and treatment claimed herein were successfully used in the development of a treatment for equine encephalitis virus. These results may facilitate the evolution of the compounds into selective and broad-spectrum anti-alphaviral drug leads.

Although the foregoing embodiment describes the claimed methods and compounds as applied in treatment development against VEEV, the methods and compounds may be widely applicable to the treatment of different alphaviral diseases, including, but not limited to, Eastern Equine Encephalitis Virus (EEEV), Western Equine Encephalitis Virus (WEEV), Chikungunya Virus (CHIKV), Sindbis Virus, Semliki Forest Virus, Barmah Forest Virus, Ross River Virus, O'nyong Virus, and Highlands J Virus.

The present invention provides compound(s) of Formula (I)

Formula I or a stereoisomer, solvate and/or pharmaceutical acceptable salt thereof; wherein
A is C(O)OR$_3$ or S(O$_2$)R$_3$;
R$_3$ is (C1-6)alkyl, (C3-7) cycloalkyl, (C3-7) cycloalkyl(C1-5)alkyl, optionally substituted aryl, or optionally substituted (C6-12)aralkyl;
R$_1$ and R$_2$ are independently selected from H, (C1-6)alkyl, (C3-7)cycloalkyl, (C3-7)cycloalkyl(C1-5)alkyl, optionally substituted aryl, or optionally substituted (C6-12) aralkyl;
R is a group selected from ---- is a single bond or double bond.

Specifically, the present invention provides compound of Formula II:

Formula II or a stereoisomer, solvate and/or pharmaceutical acceptable salt thereof;
wherein A, R$_1$, R$_2$, R$_3$ and R, are as above, more specifically in another embodiment $R_1$ is H, methyl or benzyl and $R_2$ is H or methyl.

Another embodiment of the invention provides the compound of formula (I) wherein substituents on optionally substituted aryl or optionally substituted (C6-12)aralkyl in $R_3$, $R_1$ and $R_2$ are selected from (C1-6)alkyl, (C1-6)alkoxy, halogen, halogen substituted (C1-6)alkyl, hydroxyl or amino.

In another embodiment, the invention provides a composition comprising compound of formula (I) as inhibitors of the cysteine protease domain of Venezuelan equine encephalitis virus (VEEV's) non-structural protein 2 (nsp2).

Further, the invention provides a method of treating infectious disease caused by Venezuelan equine encephalitis virus (VEEV) comprising administering a compound of Formula (I) to the patient.

The present invention further provides a compound of Formula (III)

Formula III or a stereoisomer, solvate and/or pharmaceutical acceptable salt thereof; wherein $R_4$ is (C1-6)alkyl, (C3-7)cycloalkyl, (C3-7)cycloalkyl(C1-5)alkyl, optionally substituted aryl, or optionally substituted (C6-12)aralkyl;

$R_5$ and $R_6$ are independently selected from H, (C1-6)alkyl, (C3-7)cycloalkyl, (C3-7)cycloalkyl(C1-5)alkyl, optionally substituted aryl, or optionally substituted (C6-12) aralkyl;

$R_7$ is a group selected from wherein $R_5$ is H,
wherein $R_5$ is $CH_3$,
wherein $R_5$ is benzyl,
wherein $R_6$ is H,
wherein $R_6$ is $CH_3$.

In an embodiment, the compound of formula (III) are provided wherein substituents on optionally substituted aryl or optionally substituted (C6-12)aralkyl in $R_4$, $R_5$ and $R_6$ are selected from (C1-6)alkyl, (C1-6)alkoxy, halogen, halogen substituted (C1-6)alkyl, hydroxyl or amino.

More particularly the present invention provides the compounds

In an embodiment, the invention additionally provide composition comprising compound(s) of formula (III) as inhibitors of the cysteine protease domain of Venezuelan equine encephalitis virus (VEEV's) non-structural protein 2 (nsP2).

Embodiments of the invention provide method of treating infectious disease caused by Venezuelan equine encephalitis virus (VEEV) comprising administering a compound of Formula (III) to the patient.

In an embodiment of the invention, using a library derived from a fragment-based approach to identify protease inhibitors, initial screening efforts against VEEV (IC-SH$_3$) -infected Vero and HeLa cells identified an acrylate-based 1,2-dihydroquinoline derivative, (Compound 1) as a potent VEEV inhibitor (EC50's of 0.55 µM (Vero) and 6.48 µM (HeLa)). Subsequent studies to develop SAR around compound 1 were initiated to i) understand which structural motifs are necessary for inhibition of VEEV's replication, ii) determine if the α, β-unsaturation in the acrylate warhead is crucial for inhibition (compounds 2-8), iii) determine if similar warheads like methyl vinyl sulfone and phenyl vinyl sulfone are tolerated, iv) determine the tolerability of substituents at the y-carbon, and v) determine if the dihydroquinoline heterocycle can be replaced by similar bicyclic motifs. Analogues were synthesized as outlined in FIGS. 1A, 1B and 1C.

Figure 1B:
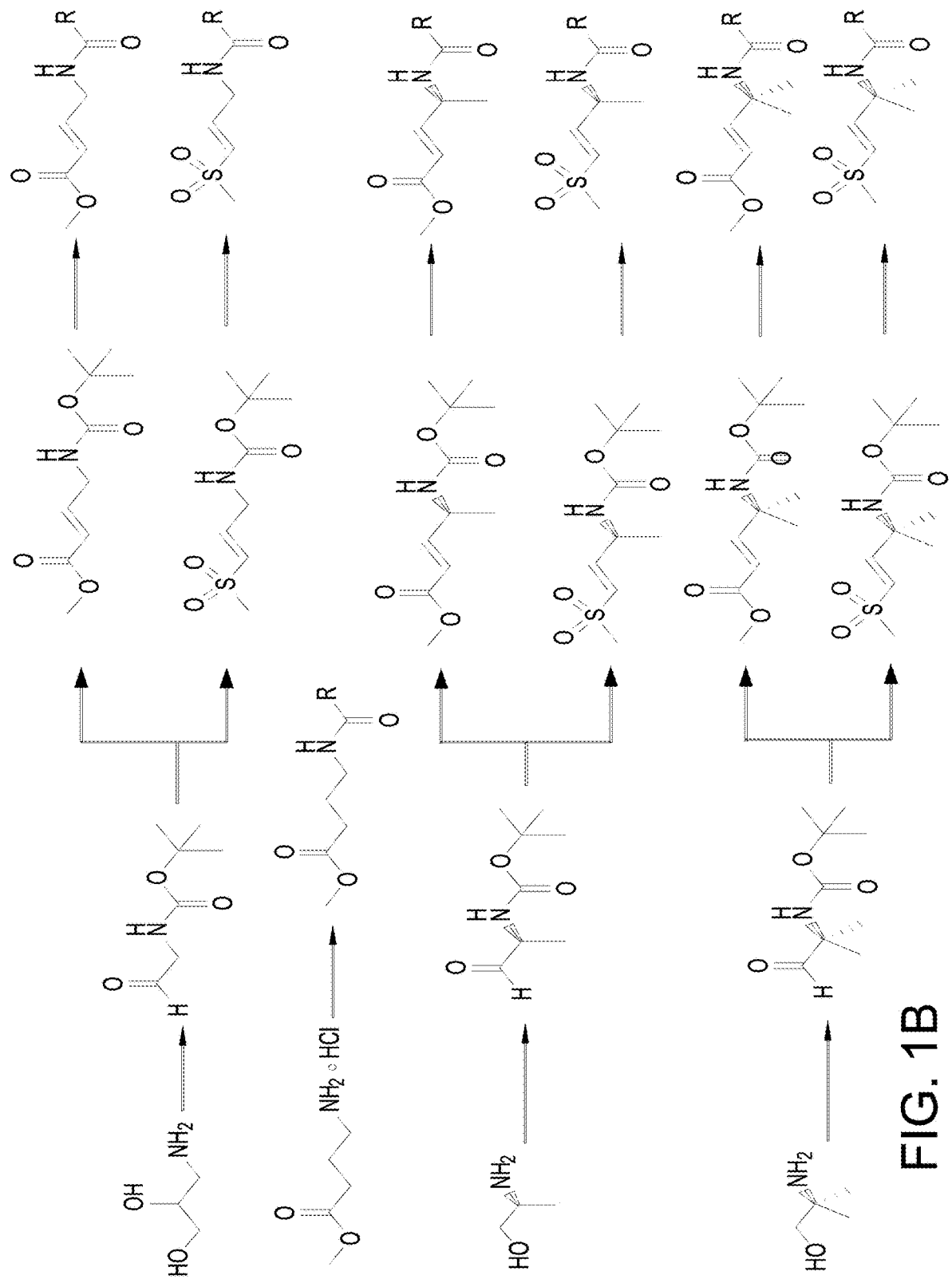
Figure 1C:
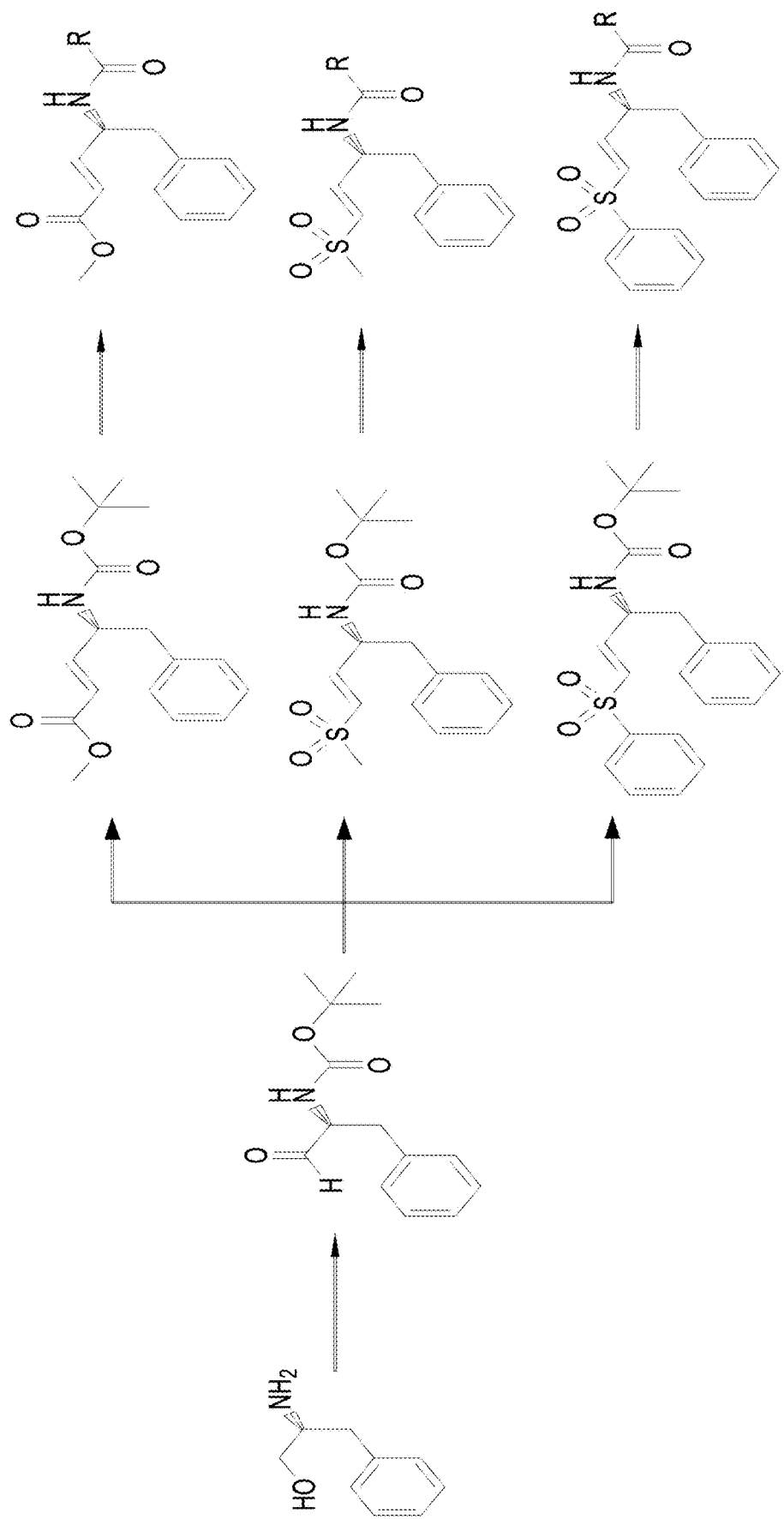

FIG. 1A illustrates the process employed for synthesis (Scheme 1) of target compounds 1-16. FIGS. 1B and 1C illustrate the process employed for synthesis (Scheme S1) of target compounds 1-43. The reagents and conditions employed in FIGS. 1A, 1B and 1C include: (a) CH$_2$Cl$_2$: CH$_3$OH (Dichloromethane methanol), Et$_3$N, Boc$_2$O (Boc-protected amino diol), 23° C., 2 hrs.; (b) H$_2$O (water), NaIO$_4$ (Sodium periodate), RT (Room Temperature), 1 h; (c) NaH (Sodium hydride), THF (Tetrahydrofuran), i, ii, or iii, 0° C., 25 min; (d) 33% TFA (Trifluoroacetic acid) in DCM (Dichloromethane), 0° C., 1.5 hrs., followed by adding ACN (Acetonitrile), Et$_3$N (Triethylamine), HBTU (2-(1h-Benzotriazole-1-yl)-1,1,3,3-tetramethyluronium hexafluorophosphate) at RT 16 h; (e) DMP (Dess-Martin periodinane), H$_2$O-DCM, 23° C., 1 hr.

FIG. 2A shows the details of the Anti-VEEV activity of compounds 1-8. The compounds were assayed from 13.72 nM-30 µM (8 doses, 3-fold dilution). HeLa and VeroE6 cells were treated with the indicated compounds and 2 hrs. later inoculated with VEEV IC-SH$_3$ (MOI=0.1 and 0.01, respectively). After 20 hrs., cells were fixed, and stained with antibodies against E2. High-content quantitative image-based analysis was used to measure relative infection rates. Compounds were assayed in VEEV IC-SH$_3$-infected BE(2)-M17 (MOI=1.2) and Neuro-2a cells (MOI=3.5).

This SAR study revealed that i) partial saturation of the dihydroquinoline ring is tolerated (2), ii) methyl substituents at the 2- and/or 4-position of the hydro-quinoline motif improve anti-VEEV activity (1 and 2 vs 4), iii) methyl substitution at carbon 6 of the 1,2-dihydroquinoline ring decreases antiviral activity, and iv) the α, β-unsaturation of the acrylate warhead is required for anti-VEEV activity (FIG. 2A -Table 1).

Subsequent analogs were evaluated against VEEV-TC$_{83}$ using neuronal cell lines including human BE(2)-M17 and mouse Neuro-2a cell lines which may be more physiologically relevant than fibroblasts. VEEV IC-SH$_3$ is a virulent strain derived from a human isolate from a VEEV outbreak in 1992-1993 in Venezuela. VEEV-TC-8$_3$ is a live-attenuated virus generated by serial passage of VEEV Trinidad (TrD) strain in guinea pig heart cells. Work with this virus can be performed in BSL$_{-2}$ and therefore, for most assays this variant was used. Substitution of the acrylate warhead with methyl sulfone (e.g., 10-13, 15) provided low micromolar potency in both neuronal cell lines.

Figure 2B:
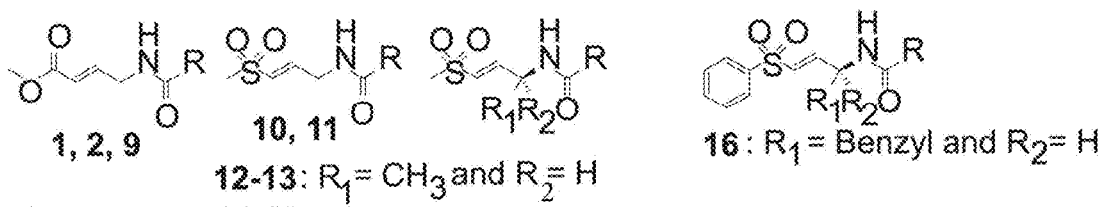
FIG. 2B shows the Anti-VEEV activity of selected analogues i.e. compounds 1, 2, 9-13.

FIG. 2B shows the Anti-VEEV activity of the selected analogues. Compounds 1, 2, 9-13 were assayed from 11.43 nM-25 µM (8 doses, 3-fold dilution) while compounds 14-16 were assayed from 22.86 nM-50 µM (8 doses, 3-fold dilution). BE(2)-M17 and Neuro-2a cells were treated with the indicated compounds and 2 hrs. later inoculated with VEEV TC8$_3$ (MOI=1.2 and 3.5, respectively). After 7 hrs., cells were fixed, and stained with antibodies against E2. High-content quantitative image-based analysis was used to measure relative infection rates. Compounds were assayed in VEEV IC-SH$_3$-infected BE(2)-M17 (MOI=1.2) and Neuro-2a cells (MOI=3.5).

The result was particularly encouraging since the methyl sulfone, as opposed to an ester, is not prone to metabolic hydrolysis. It is also interesting to note that while substitution at the y-carbon of methyl esters was not tolerated, mono-substitution of either a methyl or benzyl group on the y-carbon of sulfone derivatives retained anti-VEEV activity. Finally, it was concluded that the di- and tetrahydroquinoline moieties show specificity to VEEV inhibitory activity since replacement with either fully unsaturated quinoline or diphenylamine rings did not result in anti-VEEV activity (Table S1).

Anti-VEEV activity of compound 17-43 is shown in Table S1. BE(2)-M17 and Neuro-2a cells were treated with the indicated compounds and 2 hrs. later inoculated with VEEV TC8$_3$. After 7 hrs., cells were fixed, and stained with antibodies against E2. High-content quantitative image-based analysis was used to measure relative infection rates TABLE S1
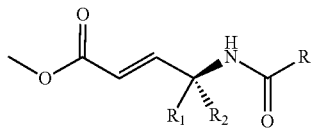 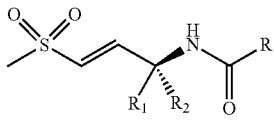 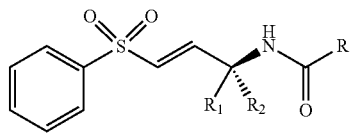
17-23: $R_1$ and $R_2$ = H
24, 25: $R_1$ = $CH_3$ and $R_2$ = H
26, 27: $R_1$ and $R_2$ = $CH_3$
28-30: $R_1$ = Benzyl and $R_2$ = H
31-35: $R_1$ = $CH_3$ and $R_2$ = H
36, 37: $R_1$ = Benzyl and $R_2$ = H
38, 39: $R_1$ and $R_2$ = $CH_3$
40-43: $R_1$ = Benzyl and $R_2$ = H
| Entry | R | Human BE(2)-M17 (TC83) | | | Mouse Neuro-2a (TC83) | | |
|---|---|---|---|---|---|---|---|
| | | $EC_{50}$ (μM) | $CC_{50}$ (μM) | SI | $EC_{50}$ (μM) | $CC_{50}$ (μM) | SI |
| 17 | 8-quinolinyl | >25.00 | >25.00 | — | >25.00 | >25.00 | — |
| 18 | 2-methyl-8-quinolinyl | >25.00 | >25.00 | — | >25.00 | >25.00 | — |
| 19 | 2-(phenylamino)phenyl | >25.00 | >25.00 | — | >25.00 | >25.00 | — |
| 20 | 2-((2,3-dichlorophenyl)amino)phenyl | >25.00 | >25.00 | — | >25.00 | 1.52 | <0.02 |
| 21 | 6-methyl-1H-indol-3-yl | >25.00 | >25.00 | — | >25.00 | >25.00 | — |
| 22 | 8-quinoxalinyl | >25.00 | >25.00 | — | >25.00 | >25.00 | — |

TABLE S1-continued

| Entry | R (structure) | Human BE(2)-M17 (TC83) EC50 (μM) | CC50 (μM) | SI | Mouse Neuro-2a (TC83) EC50 (μM) | CC50 (μM) | SI |
|---|---|---|---|---|---|---|---|
| 23 | 2-substituted phenyl-NH-(2,6-dichloro-3-methylphenyl) | >25.00 | >25.00 | — | >25.00 | 23.53 | <0.87 |

Structures (general scaffolds):

- Methyl ester scaffold (left): methyl (E)-4-(acylamino)pent-2-enoate with R₁, R₂ substituents
  - 17-23: R₁ and R₂ = H
  - 24, 25: R₁ = CH₃ and R₂ = H
  - 26, 27: R₁ and R₂ = CH₃
  - 28-30: R₁ = Benzyl and R₂ = H

- Methylsulfonyl vinyl scaffold (middle):
  - 31-35: R₁ = CH₃ and R₂ = H
  - 36, 37: R₁ = Benzyl and R₂ = H
  - 38, 39: R₁ and R₂ = CH₃

- Phenylsulfonyl vinyl scaffold (right):
  - 40-43: R₁ = Benzyl and R₂ = H

| Entry | R | Human BE(2)-M17 (TC83) | | | Mouse Neuro-2a (TC83) | | |
|---|---|---|---|---|---|---|---|
| | | EC50 (μM) | CC50 (μM) | SI | EC50 (μM) | CC50 (μM) | SI |
| 24 | 4,4,8-trimethyl-1,4-dihydroquinolin-8-yl | >25.00 | >25.00 | — | >25.00 | >25.00 | — |
| 25 | (4S)-2,2,4-trimethyl-1,2-dihydroquinolin-8-yl | >25.00 | >25.00 | — | >25.00 | >25.00 | — |
| 26 | 2,2,4-trimethyl-1,2-dihydroquinolin-8-yl | >25.00 | >25.00 | — | >25.00 | >25.00 | — |
| 27 | (4R)-2,2,4-trimethyl-1,2-dihydroquinolin-8-yl | >25.00 | >25.00 | — | >25.00 | >25.00 | — |
| 28 | 5-chloro-1H-indol-3-yl | >50.00 | >50.00 | — | >50.00 | >50.00 | — |

TABLE S1-continued

| Entry | R | EC$_{50}$ (μM) | CC$_{50}$ (μM) | SI | EC$_{50}$ (μM) | CC$_{50}$ (μM) | SI |
|---|---|---|---|---|---|---|---|
| 29 | 8-(2,2,4-trimethyl-1,2-dihydroquinolinyl) | >50.00 | >50.00 | — | >50.00 | >50.00 | — |
| 30 | 8-(2,2,4,6-tetramethyl-1,2-dihydroquinolinyl) | >50.00 | >50.00 | — | >50.00 | >50.00 | — |

17-23: R$_1$ and R$_2$ = H
24, 25: R$_1$ = CH$_3$ and R$_2$ = H
26, 27: R$_1$ and R$_2$ = CH$_3$
28-30: R$_1$ = Benzyl and R$_2$ = H 31-35: R$_1$ = CH$_3$ and R$_2$ = H
36, 37: R$_1$ = Benzyl and R$_2$ = H
38, 39: R$_1$ and R$_2$ = CH$_3$ 40-43: R$_1$ = Benzyl and R$_2$ = H

| | | Human BE(2)-M17 (TC83) | | | Mouse Neuro-2a (TC83) | | |
|---|---|---|---|---|---|---|---|
| Entry | R | EC$_{50}$ (μM) | CC$_{50}$ (μM) | SI | EC$_{50}$ (μM) | CC$_{50}$ (μM) | SI |
| 31 | 2-methylquinolin-8-yl | >25.00 | >25.00 | — | >25.00 | >25.00 | — |
| 32 | 2-(phenylamino)phenyl | >25.00 | 27.14 | 0.95 | >25.00 | >25.00 | — |
| 33 | 2-((2,3-dichlorophenyl)amino)phenyl | >25.00 | 5.86 | <0.23 | >25.00 | 15.48 | 0.62 |
| 34 | quinoxalin-5-yl | >25.00 | >25.00 | — | >25.00 | >25.00 | — |

TABLE S1-continued

| Entry | R | EC$_{50}$ (μM) | CC$_{50}$ (μM) | SI | EC$_{50}$ (μM) | CC$_{50}$ (μM) | SI |
|---|---|---|---|---|---|---|---|
| 35 | 2-(2,6-dichloro-3-methylphenylamino)phenyl | 18.23 ± 0.93 | 14.50 | >0.80 | >25.00 | >25.00 | — |
| 36 | quinolin-8-yl | >25.00 | >25.00 | — | >25.00 | >25.00 | — |
| 37 | 2,2,4,6-tetramethyl-1,2-dihydroquinolin-8-yl | 31.74 ± 16.69 | >50.00 | >1.58 | >50.00 | >50.00 | — |
| 38 | 2,2,4-trimethyl-1,2-dihydroquinolin-8-yl | >25.00 | >25.00 | — | >25.00 | >25.00 | — |

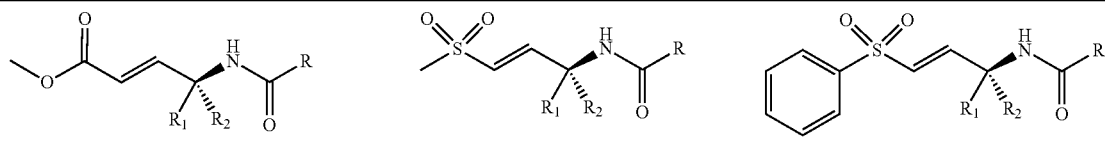

17-23: R$_1$ and R$_2$ = H
24, 25: R$_1$ = CH$_3$ and R$_2$ = H
26, 27: R$_1$ and R$_2$ = CH$_3$
28-30: R$_1$ = Benzyl and R$_2$ = H 31-35: R$_1$ = CH$_3$ and R$_2$ = H
36, 37: R$_1$ = Benzyl and R$_2$ = H
38, 39: R$_1$ and R$_2$ = CH$_3$ 40-43: R$_1$ = Benzyl and R$_2$ = H

| | | Human BE(2)-M17 (TC83) | | | Mouse Neuro-2a (TC83) | | |
|---|---|---|---|---|---|---|---|
| Entry | R | EC$_{50}$ (μM) | CC$_{50}$ (μM) | SI | EC$_{50}$ (μM) | CC$_{50}$ (μM) | SI |
| 39 | 2,2,4-trimethyl-1,2,3,4-tetrahydroquinolin-8-yl | >25.00 | >25.00 | — | >25.00 | >25.00 | — |
| 40 | 5-methoxy-1H-indol-3-yl | 23.86 ± 5.33 | >25.00 | >2.10 | >25.00 | >25.00 | — |

TABLE S1-continued

| | | | | | | | |
|---|---|---|---|---|---|---|---|
| 41 | (structure) | >25.00 | >25.00 | — | >25.00 | >25.00 | — |
| 42 | (structure) | >25.00 | >25.00 | — | >25.00 | >25.00 | — |
| 43 | (structure) | >25.00 | >25.00 | — | >25.00 | >25.00 | — |
| ML336 | Ref. S4 | 0.01 ± 0.00 | >2.50 | >250.00 | 0.02 ± 0.01 | >2.5 | >125.00 |

It is worth pointing out that different MOIs and infection times were used for the different cell lines (to achieve 50-80% infection rates at the study endpoint). These variations might have contributed to the observed $EC_{50}$ difference. Also, infection kinetics (such as the length of one virus lifecycle) might be different between the cells used. Finally, these differences might be also due to non-specific effects of the compounds on the cells. Overall, compounds 10-13 were the most active analogues in neuronal cells in the initial SAR study.

To confirm the mechanism of action for the above mentioned series of VEEV inhibitors, representative compounds were tested for their ability to inhibit the proteolytic activity of nsP2 in vitro. The protease was recombinantly expressed, purified, and assayed using the gel discontinuous assay previously reported by Legler and co-workers.

Figure 3A:
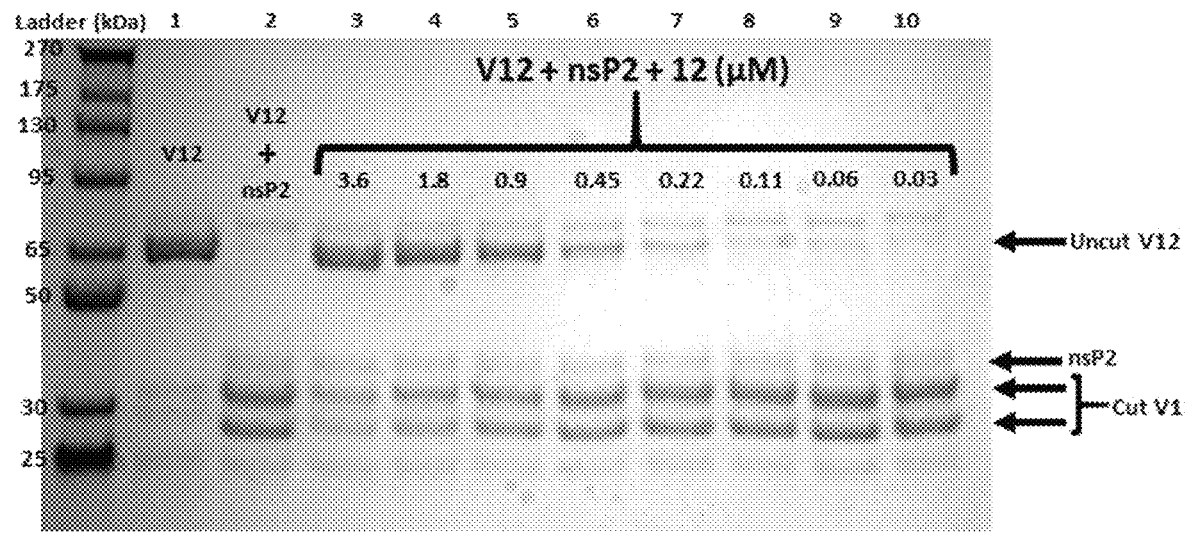
FIGS. 3A, 3B and 3C depict inhibition of VEEV nsP2 protease by compounds 12, 13 and 11 in a gel discontinuous assay.
Figure 3B:
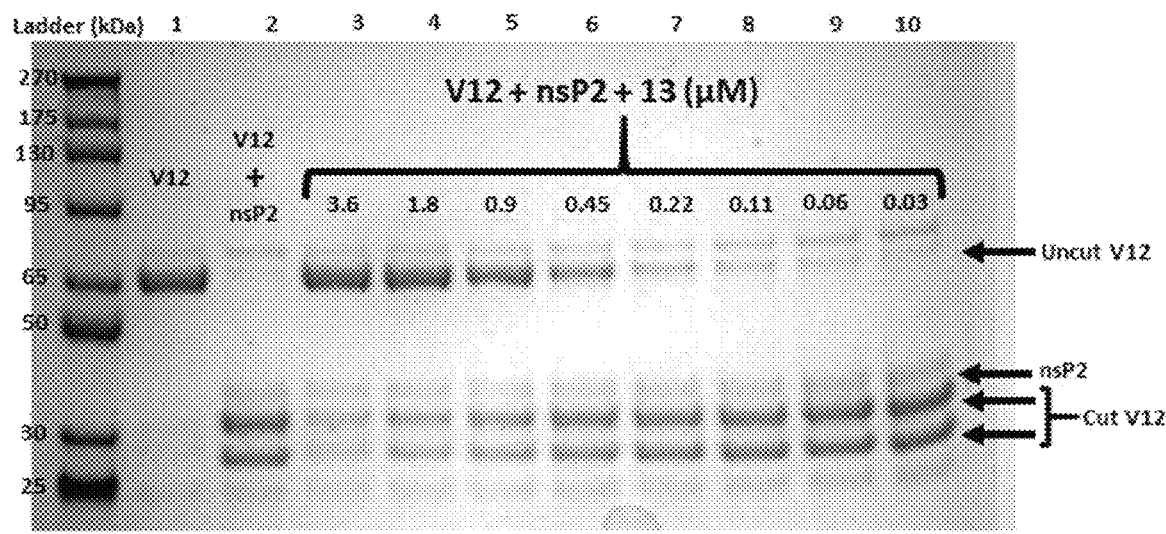
Figure 3C:
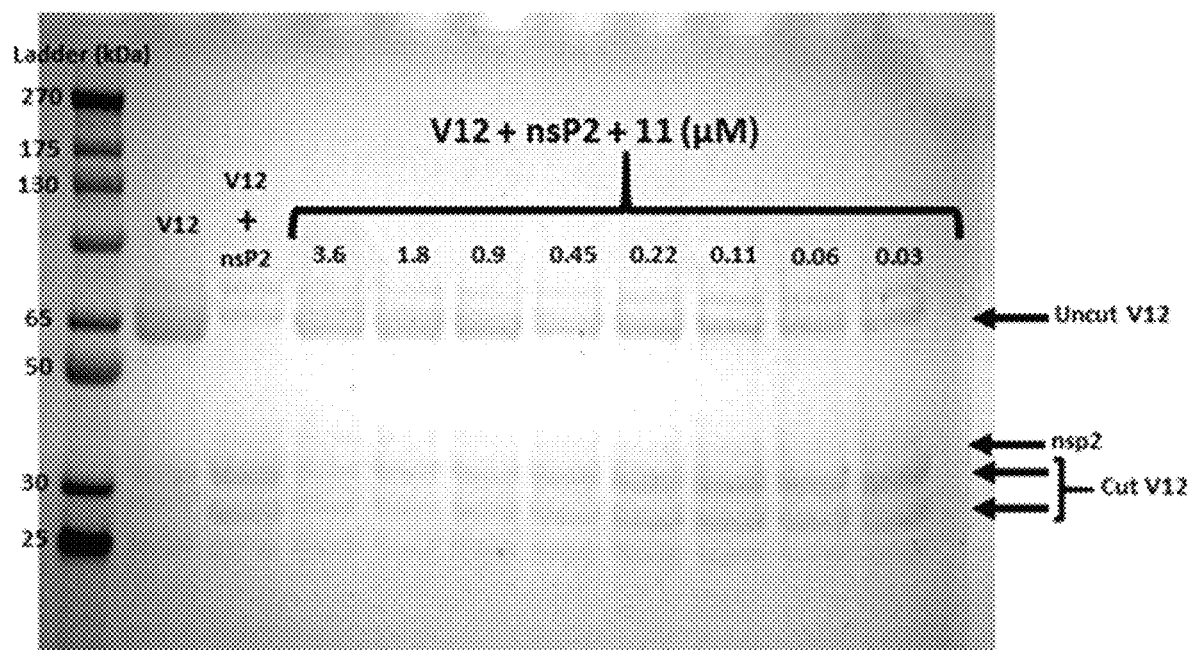

As shown in FIGS. 3A, 3B and 3C, compounds 11-13 inhibited the proteolytic activity of VEEV nsP2 in a dose-dependent manner. At 20 µM, compounds 11-13 completely inactivated VEEV nsP2 (1 µM) in the presence of $V_{12}$ substrate (a CFP-YFP FRET Substrate, 10 µM; data not shown). The estimated percentage inhibition after 24 hrs incubation was around 39%, 59% and 71% at 0.9 µM for 11, 12 and 13, respectively.

FIGS. 3A and 3B show inhibition of VEEV nsP2 protease by compounds 12 and 13 in a gel discontinuous assay. V12: CFP-YFP FRET substrate; nsP2: tag-free non-structural protease 2. For both gels, Lane 1 is V12 alone, Lane 2 is V12+nsP2, Lanes 3-10 are V12+nsP2+12 or 13 at 3.6, 1.8, 0.9, 0.45, 0.22, 0.11, 0.06 and 0.03 µM, respectively. The molecular weight (MW) of uncut V12, the two V12 fragments (cut v12) and tag-free nsP2 are 58.3, 30.9, 27.4, and 38.29 kDa, respectively. The reactions were carried out in 50 mM HEPES buffer pH 7.4 for 24 hrs at room temperature. The concentrations of VEEV nsP2 and V12 were 1 µM and 10 µM, respectively.

FIG. 3C shows inhibition of VEEV nsP2 protease by compound 11 in a gel discontinuous assay. V12: CFP-YFP FRET substrate; nsP2: tag-free non-structural protease 2. Lane 1 is V12 alone, Lane 2 is V12+nsP2, Lanes 3-10 are V12+nsP2+25 at 3.6, 1.8, 0.9, 0.45, 0.22, 0.11, 0.06 and 0.03 µM, respectively. The molecular weight (MW) of uncut V12, the two V12 fragments (cut v12) and tag-free nsP2 are 58.3, 30.9, 27.4, and 38.29 kDa, respectively. The reactions were carried out in 50 mM HEPES buffer pH 7.4 for 24 hrs at room temperature. The concentrations of VEEV nsP2 and V12 were 1 µM and 10 µM, respectively.

Figure 4:
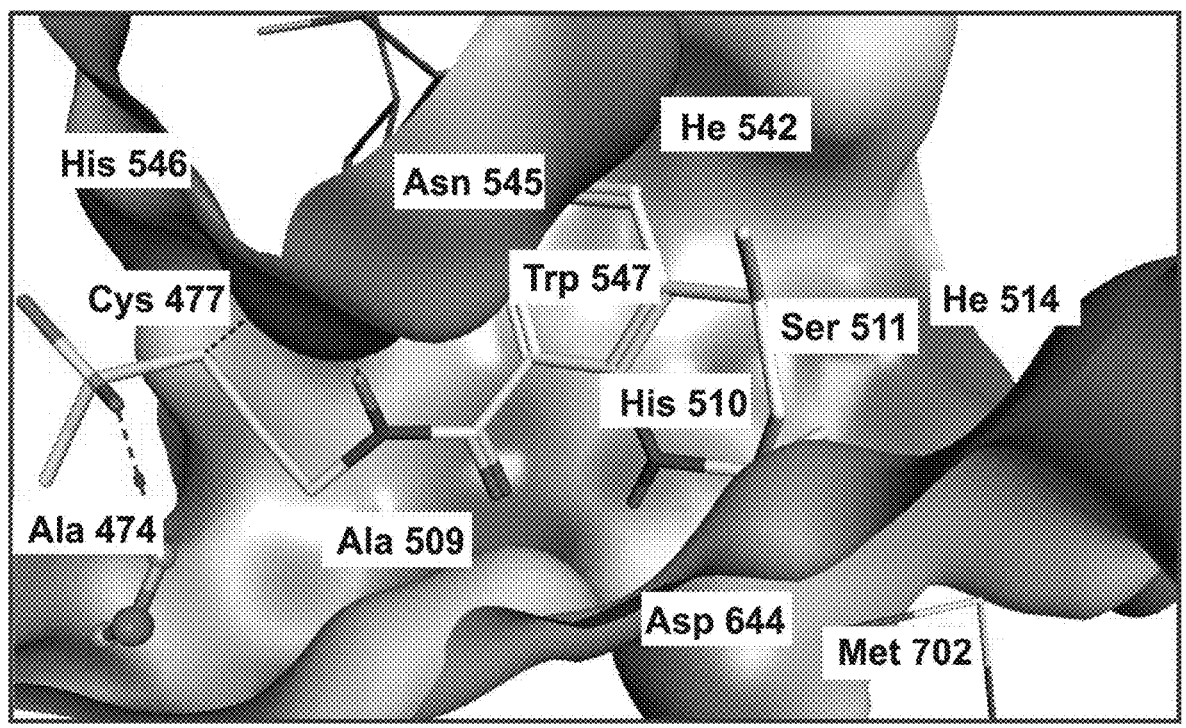
FIG. 4 shows modelled complex of VEEV nsP2 and compound 11.

Covalent molecular docking was used to predict favored binding orientations and specific binding interactions with the nsP2 protein. FIG. 4 shows modelled complex of VEEV nsP2 and compound 11. The highlighted residues are predicted to have significant Van der Waals interactions (piecewise linear potential) with compound 11. The blue dash depicts H-bond interaction. FIG. 4 was prepared using Molecular Operating Environment (MOE). As shown in FIG. 4, compound 11 was predicted to have significant Van der Waals interactions with Trp 547, Asn 545, Asn 475, Ala 509, and His 510, and complex-stabilizing hydrogen bonding interactions with Asn 545, His 510 and a key water molecule within the active site. The methyl sulfone motif as well as methyl substituents of the tetrahydroquinoline ring are predicted to be partially exposed to solvent, and thus these moieties may provide an avenue for physicochemical property modifications. Co-crystallization of nsP2 with selected inhibitors, in order to determine the preferred binding modes of the compounds, is under active investigation.

Figure 5B:
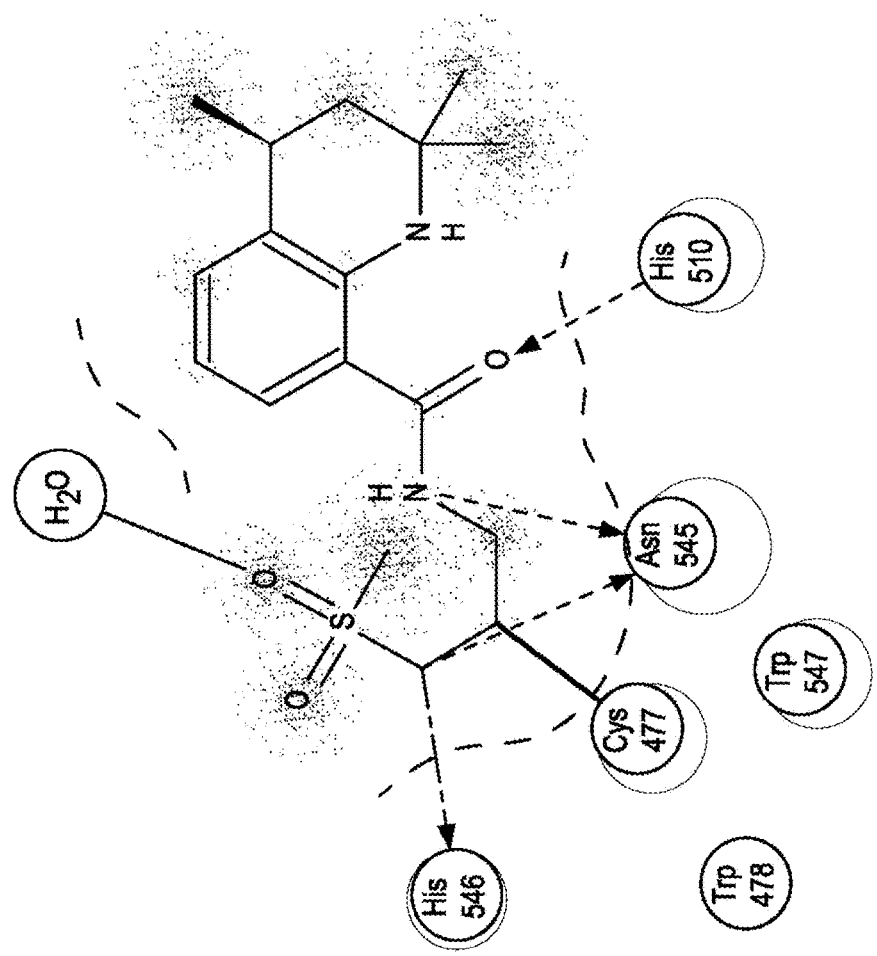
FIGS. 5A and 5B show modelled complex (stick model) of VEEV nsP2 and compound 11.
Figure 5A:
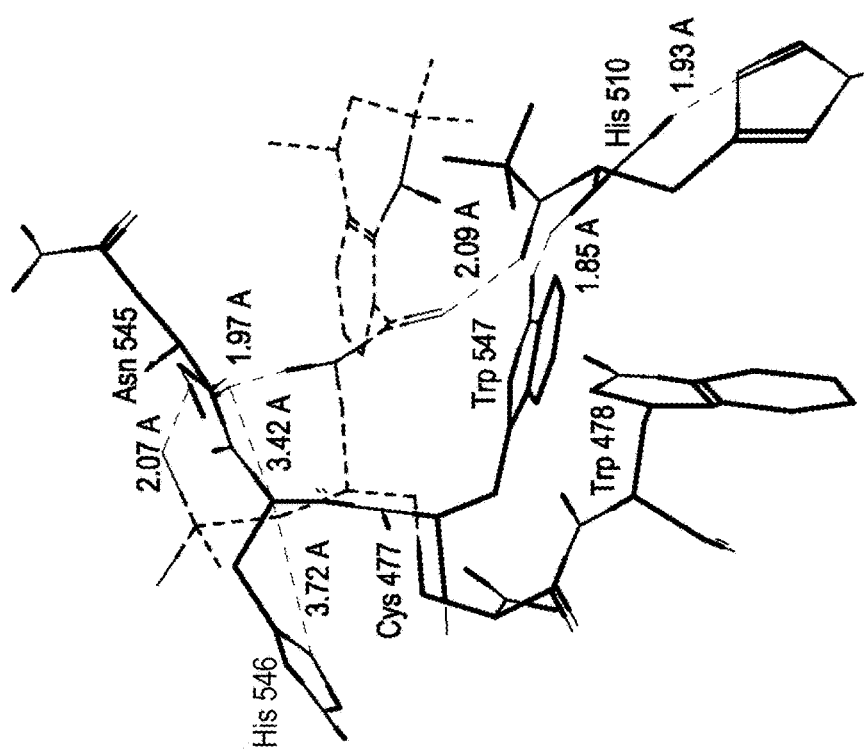

Further, FIGS. 5A and 5B show Modelled complex (stick model) of VEEV nsP2 and compound 11. The left panel shows a stick model representation of the predicted network of H-bond interactions (depicted as dash lines) stabilizing the nsp2-11 complex. Asn 545, His 510 and His 546 residues are predicted to have direct H-bond interactions with compound 11. Carbon atoms are depicted as black in 11. The right panel is a 2D depiction of the proximity (dotted contour lines) of active site residues to compound 11 as well as the extent of exposure (black dots) of the compound's atoms to solvent. FIGS. 5A and 5B were prepared using Molecular Operating Environment (MOE).

In summary, a new series of nonpeptidic dihydroquinoline and tetrahydroquinoline-based covalent inactivators of VEEV's nsP2 cysteine protease were identified as part of the ongoing disclosure. The preliminary SAR study depicted that the conformationally more flexible dihydroquinoline and tetrahydroquinoline rings provide an appropriate shape for effective binding at the active site. Ongoing and future work will define any absorption, distribution, metabolism, and excretion (ADME) issues and focus on optimization of the hit compounds.

Figure 6:
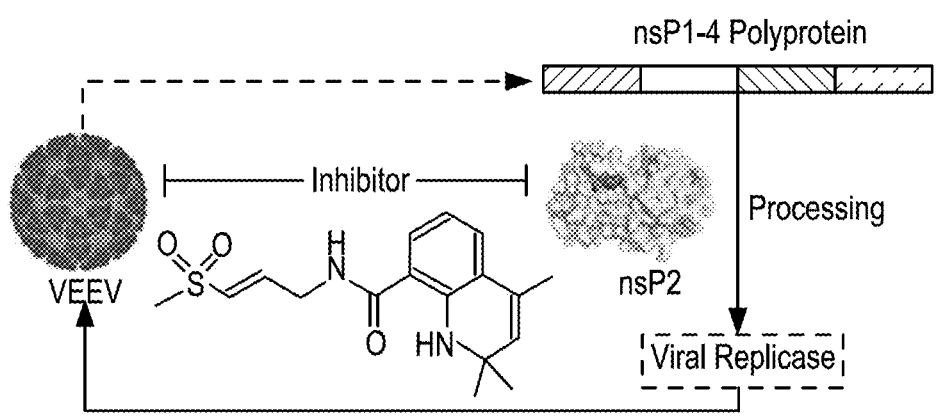
FIG. 6 depicts the exemplary mechanism of action of the vinyl sulfone inhibitors of the present invention.

FIG. 6 shows the mechanism of action of the vinyl sulfone inhibitors i.e. the compounds of the present invention for use in the treatment of Venezuelan equine encephalitis virus's (VEEV).

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

1. Bioassays
a) Antiviral Assay:

Primary screen: HeLa cells were plated 24 hours before compound treatment at 2,000 cells/well in 35 µL of culture media/well in imaging 384 well assay plates (Aurora 384, IQ-EB, 384 IQ-EB/NB, 200 m clear, #1052-11130). Two hundred compounds were screened in 2 replicates at 4 final concentrations (0.24, 1.2, 6, and 30 µM) using 100×compound stocks in 100% DMSO stored on 384 well source plates. Compounds were diluted in media to generate a 10×intermediate concentration using the Perkin Elmer Janus Modular Dispense Technology platform with 384—tip head and 5 µL of diluted compound were transferred immediately into the assay plates containing HeLa cells. At least one control compound was also included for internal quality control. DMSO concentration in all wells was normalized to 1%. Two hours post compound treatment, assay plates were transferred to BSL-3 suites for VEEV (IC-SH$_3$) infection (MOI=0.2, 10 µL of virus mix/well). Cells were fixed in 10% formalin 24 hrs post virus inoculation.

Dose Responses: For EC$_{50}$ and CC$_{50}$ determination, the HP-D300 digital dispenser was used to generate 8-point dose response with a 3-fold step dilution. Each dose was dispensed in triplicate. For each 384 well plate, one or two control compounds were used for quality control. DMSO concentration in all wells was normalized to 0.5-1%. VeroE6 (4,000 cells/well), HeLa (5,000 cells/well), human BE(2)-M17 (6,000 cells/well) and mouse Neuro-2a cells (6,000 cells/well) were seeded similarly to the primary screen, one day prior to virus inoculation. Cells were infected with VEEV IC-SH$_3$ at MOI=0.01 (VeroE6) or 0.1 (HeLa). BE(2)-M17 and Neuro-2a cells were infected with VEEV-TC8$_3$ at MOI of 1.2 and 3.5, respectively. Cells were fixed in 10% formalin 20 hrs (VEEV IC-SH$_3$) or 7 hrs (VEEV-TC8$_3$) post virus inoculation. In some dose responses, Neuro-2a cells were infected with VEEV-TC8$_3$ at a MOI of 0.005 and fixed in 10% formalin 20 hrs post virus inoculation.

Immunostaining: Detection and quantification of viral infection in assay plates was performed using a high-content imaging (HCI) assay to measure viral antigen production after immunofluorescent labelling. To detect viral infection, inactivated plates were transferred into BSL-2 lab for immunostaining Assay wells were incubated with permeabilization/blocking buffer containing 3% BSA/0.1% Trition/PBS for 1 hr. Assay wells were then stained for 1 hr with a primary antibody against VEEV E2 (mm 1A4A) diluted 1,000-fold in blocking buffer. Following incubation, the primary antibody was removed, and the cells washed 3 times with 1×PBS. Cells were subsequently incubated for 1 hr with DyLight-488-conjugated goat anti-mouse IgG (Thermo Fisher, #35502B), diluted 1,000-fold in blocking buffer. Cells were also stained with Hoechst3332 (Thermo Fisher) for nuclei detection and CellMask Deep Red (Thermo Fisher, #C10046) for optimal detection of cytoplasm for at least 30 min before image acquisition.

Image and data analysis: Images were acquired on the Opera confocal imaging instrument (Perkin Elmer) using 10×Air objective (five fields were acquired per each well). Signal from virus staining was detected by CCD cameras at 488 nm emission wavelength, nuclei staining at 400 nm and cytoplasm staining at 640 nm. Image analysis was performed simultaneously with image acquisition using PE Acapella algorithms. The assay quality of each plate was assessed using the Z' (Z prime factor). Assay results were considered acceptable if Z'>0.5. Additionally, the % infection rate, consistency of cell counts per well and results for internal positive control compounds were also used as a quality control criteria for each plate. Dose response curve analysis (to determine EC$_{50}$ values) was performed using GeneData Screener software applying Levenberg-Marquardt algorithm (LMA) for curve-fitting strategy. Most of the curve-fittings were done using 2-, 3- or 4-parameter non-linear regression. Fitting strategy was considered acceptable if a conversion produced R$^2$>0.8.

b. Recombinant Expression and Assay of VEEV nsP2 and V12 Substrate

I. Expression and Purification: VEEV nsP2 and V12 were expressed in E. coli (BL-21(DE3)) as reported by Hu and co-workers with some modifications. Fresh 4×800 µL cultures of E. coli (BL-21(DE3)), from 1 mL transformation/expression culture screens, were used to inoculate 4×500 mL of LB media containing 50 µg/mL ampicillin and 0.25 µg/mL chloramphenicol. The cultures were grown to an OD600 of approximately 0.8 (about 6 h) and induced with 0.5 mM isopropyl β-D-1-thiogalactopyranoside (IPTG) overnight at 17° C. The cells were pelleted and stored at −20° C. or lysed for immediate purification. Cell lysis was carried out using 50 mM Tris, pH 7.6, 500 mM NaCl, 5% glycerol, 2 mM BME, bugbuster reagent, and lysonase. The lysates were sonicated 6 times for 30 second intervals. Lysates were clarified by centrifugation at 4,600 rpm for 30 minutes. The lysates were loaded onto Ni-NTA columns equilibrated with 50 mM Tris, pH 7.6, 500 mM NaCl, 2 mM BME, 5% glycerol, 15 mM imidazole. The column was then washed with 20 column volumes of the equilibration buffer, followed by the same buffer containing 30 mM imidazole. The proteins were eluted using the same buffer containing 300 mM imidazole. VEEV nsP2 was dialyzed overnight at 4° C. against 50 mM Tris pH 7.6, 250 mM NaCl, 5 mM dithiothreitol (DTT), 10% glycerol. The partially purified VEEV nsP2 was then incubated with thrombin sepharose beads (Biovision) at 12° C. for 42 hrs to remove the thioredoxin tag. The thrombin sepharose beads were sedimented at 2000 rpm for 3 minutes, and the supernatant was loaded onto Ni-NTA column equilibrated with 50 mM Tris, pH 7.6, 500 mM NaCl, 2 mM BME, 5% glycerol, 15 mM imidazole. The column was washed successively with the equilibration buffer containing 15 mM (2×10 mL), 30 mM (2×10 mL), and 300 mM (2×10 mL), as described above. The tag-free VEEV nsP2 protease was found in the flow through and in fractions eluted with 15 mM imidazole. The fractions were pooled, dialyzed against 50 mM Tris pH 7.6, containing 250 mM NaCl, 5 mM dithiothreitol (DTT), and 10% glycerol, flash frozen, and stored at −80° C. The V12 substrate was dialyzed against 50 mM Tris (pH 7.6) and 150 mM NaCl overnight at 4° C. and further purified on a Q-sepharose column. The sepharose column was equilibrated and washed with 50 mM Tris (pH 7.6) buffer containing 150 mM NaCl. The V12 substrate was in the flow through. The substrate fractions were pooled, flash frozen and stored at −80° C.

II. Discontinuous Gel Assay: VEEV nsP2 and V12 were buffer exchanged into 50 mM HEPES buffer pH 7.4, and the protein concentrations were adjusted to 1 µM and 10 µM, respectively. The inhibitors, 11-13 (30 mM in DMSO) were serially diluted with HEPES buffer to prepare stock solutions: 100 µM, 50 µM, 25 µM, 12.5 µM, 6.25 µM, 3.13 µM, 1.56 µM, and 0.78 µM. The assay mixtures were prepared using 44 µL of 10 µM V12 substrate, 10 µL of 1 µM VEEV nsP2, and 2 µL of inhibitors at different concentrations, in a half area 96-well plate. The plate was sealed, and the mixtures were incubated for 24 hrs at room temperature. Subsequently, 20 µL of SDS sample buffer was mixed with 20 µL of each reaction mixture, heated for 10 minutes at 70° C., and allowed to cool on ice. The protein samples were resolved on 4-12% SDS-PAGE gels (SurePAGE, Bis-Tris, GenScript) using Tris-MOPS SDS Running buffer. The gels were imaged on a Bio-Rad Gel Doc Imager and the bands were quantified using NIH Image J.

2. Covalent Docking

Ligand structures were built with MOE '18 for Windows and their geometries were optimized using the AMBER 10:EHT force field. The docking simulations were carried out using the covalent docking option in MOE '18. Michael acceptor/vinyl sulfone and 1,4-addition/Michael addition were selected as functional group and reaction class, respectively. Both rigid receptor and induced fit refinements were used. The force constant for refinements was set to 100 with radius offset of 0.4, gradient of 0.01, and 500 iterations. The number of pose placements was set to 30 while 5 poses were retained. The complexes were visually inspected and analyzed with MOE and Molegro Virtual Docker. The 2D & 3D representation of protein-ligand complex was prepared using MOE '18.

3. Exemplary Synthesis and Product Characterization Data of the Compounds/Analogues of the Present Invention The compounds were synthesized as shown in FIGS. 1A and 1B. Reagents were purchased from commercial sources and used without further purification. $^1$H and $^{13}$C NMR spectra were recorded on Varian 500 MHz. FIG. 1B depicts synthesis of target compounds 1-43. Reagents and conditions used for synthesis include (a) $CH_2Cl_2$:$CH_3OH$, $Et_3N$, $Boc_2O$, 23° C., 2 h; (b) $H_2O$, $NaIO_4$, RT, 1 hr; (c) NaH, THF, i, ii, or iii, 0° C., 25 min; (d) 33% TFA in DCM, 0° C., 1.5 hrs. Then ACN, $Et_3N$, HBTU, RT, 16 h; (e) DMP, $H_2O$-DCM, 23° C., 1 hr.

Agilent Inova 500 (Agilent, Santa Clara, Calif., USA) and Bruker Ultrashield Avance 400 (Bruker, Billerica, Mass., USA) spectrometers were used to conduct NMR analysis of the compounds. Thin layer chromatography (TLC) and NMR were used to monitor reactions, and purification conditions. Compounds were purified by column chromatography on silica gel or on pre-coated preparative TLC plates. Accurate mass information was obtained on Synapt G2 HDMS instrument operated in positive or negative ESI mode. HPLC-UV analysis was carried out on a Shimadzu Prominence HPLC-UV system using isocratic elution with 90% MeOH, 5% ACN, and 5% $H_2O$ (Pinnacle II C18 5 µM, 200×4.6 mm column; flowrate=0.5 mL/min).

Synthesis of S2

(±)-3-amino-1,2-propanediol (S1, 11.29 g, 124 mmol) was dissolved in $CH_2Cl_2$:$CH_3OH$ (1:5; 1 M) and triethylamine (2 mL, 14.7 mmol) was added. Di-tert-butyl dicarbonate (32.5 g, 149 mmol) was dissolved in dichloromethane (0.8 M, 186 mL) and added slowly to the reaction mixture. The resulting reaction was stirred at 23° C. for 2 hrs followed by TLC analysis that showed full consumption of the starting material. The reaction mixture was evaporated under reduced pressure, and the residue was purified by column chromatography with EtOAc:hexanes 1:4, then dried on high vacuum to yield the Boc-protected amino diol as a white solid (21.82 g, 92% yield). The Boc-protected amino diol (21.82 g, 113 mmol) was suspended in $H_2O$ (0.6M, 190 mL) and the flask was covered in foil (to protect $NaIO_4$ from light). $NaIO_4$ (29.2 g, 137 mmol) was then added and the reaction was stirred for 1 hr. A white precipitate had formed after 1 hr, and TLC analysis showed full consumption of the starting material. The precipitate was filtered, and the aqueous layer was extracted with $CHCl_3$ (8×50 mL). The organic layer was dried with $MgSO_4$, filtered, and evaporated to yield S2 as a light-yellow oil, which was used without further purification (12.65 g, 64% yield).

Compound S2—Characterization

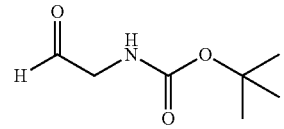

$^1$ H NMR (500 MHz, CDCl$_3$) δ 9.62 (s, 1H), 5.26 (s, 1H), 4.04 (d, J=6.5 Hz, 2H), 1.43 (s, 9H).

General Method for Synthesis of S7, S10, and S15

S6, S9 and S14 were Boc-protected and extracted as described above. Dess-Martin periodinane (5.25 mmol) was added to a solution of the Boc-protected amino alcohols (2.5 mmol) in water-saturated dichloromethane (20 mL). The resulting suspension was stirred at 23° C., and the progress of the reaction was monitored by TLC. Additional 10 mL portions of water-saturated dichloromethane were added (three portions over 15 min) once the rate of conversion has slowed considerably. After 25 min, no remaining starting materials were detected by TLC, and the reaction mixtures were diluted with diethyl ether (40 mL) followed by the addition of a solution of sodium thiosulfate (11 mol eq) in 80% saturated aqueous sodium bicarbonate solution (40 mL). The mixtures were stirred rapidly for 10 min until both phases were clear. Once the layers were separated, the aqueous layer was extracted two more times with diethyl ether. The organic layers were evaporated under reduced pressure. The residue was purified by column chromatography and dried to yield S7, S10, and S15 (40-60% yield).

Compound S7—Characterization

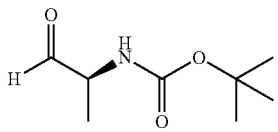

¹H NMR (500 MHz, CDCl₃) δ 9.56 (s, 1H), 5.11 (s, 1H), 4.23 (s, 1H), 1.45 (s, 9H), 1.33 (d, J=7.5 Hz, 3H).

Compound S10—Characterization

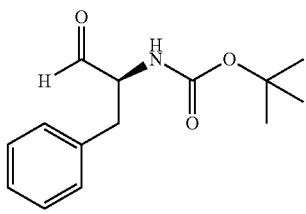 [SMILES: CC(C)(C)OC(=O)N[C@H](C=O)Cc1ccccc1]

¹H NMR (500 MHz, CDCl₃) δ 9.63 (s, 1H), 7.31 (t, J=7.5 Hz, 2H), 7.25 (t, J=7.5 Hz, 1H), 7.17 (d, J=7.5 Hz, 2H), 5.05 (s, 1H), 4.44 (m, 1H), 3.11 (d, J=6.5 Hz, 2H), 1.43 (s, 9H).

Compound S15—Characterization

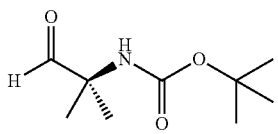

¹H NMR (500 MHz, CDCl₃) δ 9.42 (s, 1H), 4.99 (s, 1H), 1.43 (s, 9H), 1.32 (s, 6H).

General Method for the Synthesis of S3, S4, S8, S11-13, S16-S18

Sodium hydride (1.5 eq)-tetrahydrofuran (THF) solutions were cooled to 0° C., methyl diethylphosphonoacetate (i), diethyl ((methylsulfonyl)methyl) phosphonate (ii) or diethyl ((phenylsulfonyl)methyl) phosphonate (iii), in THF was added dropwise (1.0 eq). The reactions were stirred at 0° C. for 20 min. Thereafter, compounds S2, S7, S10, and S15 (1.0 eq) in THF were added. After stirring for 5 minutes, the reactions were quenched with saturated aqueous solution of sodium bicarbonate. The mixtures were diluted with ethyl acetate and water. The layers were separated, and the aqueous layers were extracted with ethyl acetate (3 times). The organic layers were dried over MgSO₄, filtered, and evaporated. The mixtures were purified by flash column chromatography to obtain compounds S3, S4, S8, S11-13, S16-S18 (40-70% yield).

Compound S3—Characterization

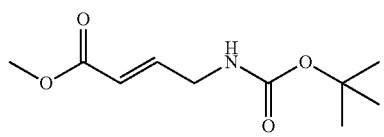

¹H NMR (500 MHz, CDCl₃) δ 6.92 (dt, J=15.5 Hz, J=5.0 Hz, 1H), 5.94 (dt, J=15.5 Hz, J=1.5 Hz, 1H), 4.73 (s, 1H), 3.92 (s, 2H), 3.73 (s, 3H), 1.44 (s, 9H).

Compound S4 Characterization

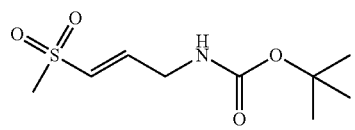

¹NMR (500 MHz, CDCl₃) δ 6.81 (dt, J=19.0 Hz, J=5.5 Hz, 1H), 6.44 (d, J=18.5 Hz, 1H), 5.25 (t, J=7.5 Hz, 1H), 3.90 (s, 2H), 2.87 (s, 3H), 1.37 (s, 9H).

Compound S8 Characterization

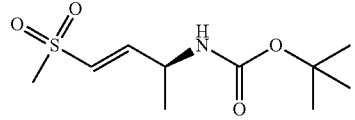 [SMILES: C[C@@H](/C=C/S(C)(=O)=O)NC(=O)OC(C)(C)C]

¹H NMR (500 MHz, CDCl₃) δ 6.84 (dd, J=15.0 Hz, J=5.0 Hz, 1H), 6.55 (dd, J=15.0 Hz, J=1.5 Hz, 1H), 4.65 (d, J=7.0 Hz, 1H), 4.45 (s, 1H), 2.93 (s, 3H), 1.43 (s, 9H), 1.29 (d, J=7.0 Hz, 3H).

Compound S11 Characterization

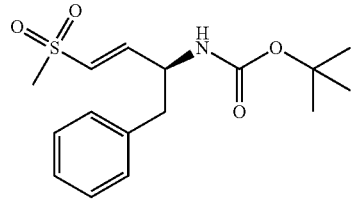 [SMILES: CC(C)(C)OC(=O)N[C@H](/C=C/S(C)(=O)=O)Cc1ccccc1]

¹H NMR (500 MHz, CDCl₃) δ 7.29 (t, J=7.5 HZ, 2H), 7.22 (t, J=7.5 Hz, 1H), 7.16 (d, J=7.5 Hz, 2H), 6.91 (dd, J=15.5 Hz, J=5.0 Hz, 1H), 5.85 (d, J=16.0 Hz, 1H), 4.64 (t, J=7.5 Hz, 1H), 4.60 (s, 1H), 3.70 (s, 3H), 2.87 (d, J=5.5 Hz, 2H), 1.38 (s, 9H).

Compound S12 Characterization

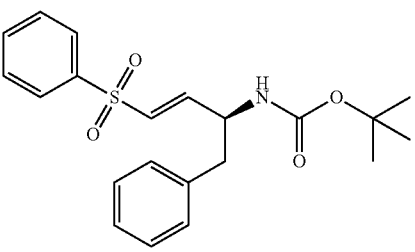 [SMILES: CC(C)(C)OC(=O)N[C@H](/C=C/S(=O)(=O)c1ccccc1)Cc1ccccc1]

¹H NMR (500 MHz, CDCl₃) δ 7.81 (d, J=7.5 Hz, 2H), 7.61 (t, J=7.5 Hz, 1H), 7.52 (t, J=7.5 Hz, 2H), 7.28-7.21 (m, 3H), 7.11 (d, J=7.0 Hz, 2H), 6.93 (dd, J=15.0 Hz, J=5.0 Hz, 1H), 6.32 (dd, J=15.0 Hz, J=1.5 Hz, 1H), 4.66 (s, 1H), 4.52 (s, 1H), 2.87 (d, J=6.0 Hz, 2H), 1.35 (s, 9H).

Compound S13 Characterization

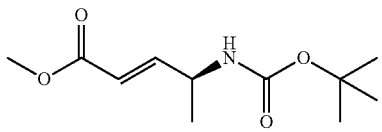 [SMILES: COC(=O)/C=C/[C@H](C)NC(=O)OC(C)(C)C]

¹H NMR (500 MHz, CDCl₃) δ 6.86 (dd, J=15.5 Hz, J=4.5 Hz, 1H), 5.88 (dd, J=15.5 Hz, J=1.5 Hz, 1H), 4.58 (s, 1H), 4.38 (s, 1H), 3.71 (s, 3H), 1.42 (s, 9H), 1.24 (d, J=7.0 Hz, 3H).

Compound S16 Characterization

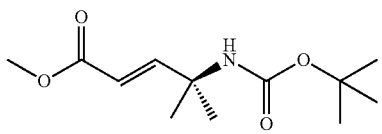

¹H NMR (500 MHz, CDCl₃) δ 6.98 (d, J=16.0 Hz, 1H), 5.82 (d, J=15.5 Hz, 1H), 4.69 (s, 1H), 3.70 (s, 3H), 1.39 (s, 9H), 1.37 (s, 6H).

Compound S17 Characterization

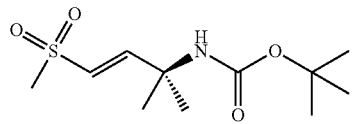

¹H NMR (500 MHz, CDCl₃) δ 6.92 (d, J=15.0 Hz, 1H), 6.38 (d, J=15.0 Hz, 1H), 4.73 (s, 1H), 2.94 (s, 3H), 1.42 (s, 15H).

Compound S18 Characterization

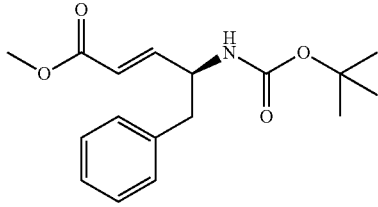 [SMILES: COC(=O)/C=C/[C@H](Cc1ccccc1)NC(=O)OC(C)(C)C]

¹H NMR (500 MHz, CDCl₃) δ 7.28 (t, J=7.5 HZ, 2H), 7.21 (t, J=7.0 Hz, 1H), 7.15 (d, J=7.5 Hz, 2H), 6.90 (dd, J=16.0 Hz, J=5.0 Hz, 1H), 5.85 (d, J=15.5 Hz, 1H), 4.69 (d, J=9.0 Hz, 1H), 4.60 (s, 1H), 3.69 (s, 3H), 2.87 (d, J=6.0 Hz, 2H), 1.37 (s, 9H).

General Method for the Synthesis of 1-4, 9-43

Compounds S3, S4, S8, S11-13, S16-S18 (0.1 mmol) were dissolved in 33% TFA-dichloromethane solution (1.5 mL) and allowed to stir at 0° C. for 1.5 hrs. The solutions were concentrated and washed twice with 5 mL toluene to remove any remaining TFA. The deprotected amines were re-dissolved in 2 mL of anhydrous acetonitrile and the corresponding acids (0.10 mmol), Et₃N (31 µL, 0.218 mmol) and HBTU (41.7 mg, 0.11 mmol) were added. The solutions were allowed to stir overnight. The reactions were quenched with brine (5 mL). The aqueous layers were extracted three times with 10 mL of ethyl acetate. The extracts were concentrated, and the amides were purified on prep-TLC plates using EtOAc:hexanes 2:1 (30-40% yield).

General Method for Synthesis of 5-8

Methyl-4-aminobutyrate hydrochloride (S5, 0.23 mmol) was dissolved in 4×2 mL of anhydrous acetonitrile and corresponding acids (0.23 mmol), Et₃N (65 µL, 0.457 mmol) and HBTU (41.7 mg, 0.23 mmol) were added. The solutions were allowed to stir overnight. The mixtures were concentrated and purified on prep-TLC plates using EtOAc:hexanes 2:1 to obtain the amides (30-40% yield).

Compound 1 Characterization

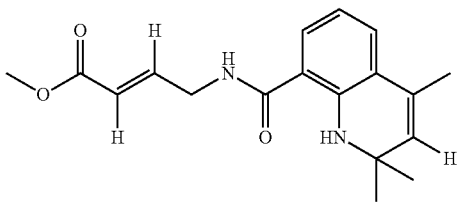 [SMILES: COC(=O)/C=C/CNC(=O)c1cccc2c1NC(C)(C)C=C2C]

¹H NMR (500 MHz, CDCl₃) δ 7.98 (s, 1H), 7.17 (d, J=8.0 Hz, 1H), 7.11 (d, J=7.5 Hz, 1H), 7.00 (dt, J=15.5 Hz, J=5.0 Hz, 1H), 6.47 (t, J=8.0 Hz, 1H), 6.22 (s, 1H), 5.99 (dt, J=15.5 Hz, J=1.5 Hz, 1H), 5.35 (s, 1H), 4.19 (m, 2H), 3.73 (s, 3H), 1.97 (d, J=1.0 Hz, 3H), 1.32 (s, 6H). ¹³C NMR (125 MHz, CDCl₃) δ 169.6, 166.6, 146.2, 144.6, 129.1, 127.5, 127.0, 126.2, 122.9, 121.5, 114.1, 111.5, 51.8, 51.7, 40.3, 32.2, 19.2. HRMS [M-H]⁺ calculated for C₁₈H₂₃N₂O₃: 315.1709; found: 315.1705. HPLC-UV: 97.8%.

Compound 2 Characterization

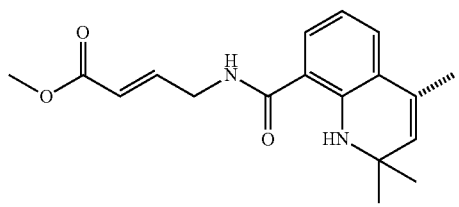

¹H NMR (500 MHz, CDCl₃) δ 7.76 (s, 1H), 7.24 (d, J=7.5 Hz, 1H), 7.20 (d, J=8.0 Hz, 1H), 7.00 (dt, J=15.5 Hz, J=5.0 Hz, 1H), 6.50 (t, J=7.5 Hz, 1H), 6.24 (s, 1H), 5.99 (dt, J=15.5 Hz, J=2.0 Hz, 1H), 4.18 (m, 2H), 3.73 (s, 3H), 2.91 (m, 1H), 1.73 (dd, J=12.5 Hz, J=5.0 Hz, 1H), 1.40 (t, J=12.5 Hz, 1H), 1.34 (d, J=6.5 Hz, 3H), 1.29 (s, 3H), 1.21 (s, 3H). ¹³C NMR (125 MHz, CDCl₃) δ 170.1, 166.6, 146.3, 144.7, 130.1, 127.4, 125.2, 121.4, 113.7, 112.3, 51.8, 49.0, 43.4, 40.3, 31.6, 29.0, 27.8, 20.3. HRMS [M-H]⁺ calculated for C₁₈H₂₅N₂O₃: 317.1865; found: 317.1869. HPLC-UV: 95.5%.

Compound 3 Characterization

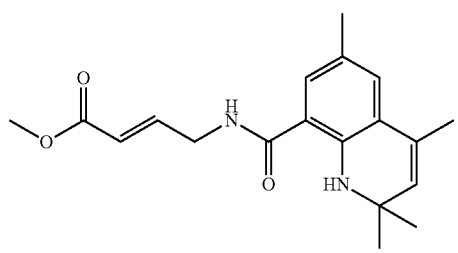

¹H NMR (500 MHz, CDCl₃) δ 7.76 (s, 1H), 7.00 (dt, J=19.5 Hz, J=6.5 Hz, 1H), 6.98 (s, 1H), 6.94 (s, 1H), 6.25 (t, J=7.0 Hz, 1H), 5.98 (dt, J=19.5 Hz, J=2.5 Hz, 1H), 5.36 (s, 1H), 4.18 (m, 2H), 3.73 (s, 3H), 2.20 (s, 3H), 1.96 (d, J=1.5 Hz, 3H), 1.29 (s, 6H). ¹³C NMR (125 MHz, CDCl₃) δ 169.3, 166.4, 144.5, 129.5, 128.0, 127.5, 126.1, 121.3, 51.66, 40.2, 31.4, 20.6, 19.0. HRMS [M-H]⁺ calculated for $C_{19}H_{25}N_2O_3$: 329.1865; found: 329.1866. HPLC-UV: 98.4%.

Compound 4 Characterization

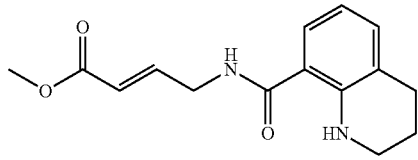 [SMILES: COC(=O)/C=C/CNC(=O)c1cccc2c1NCCC2]

¹H NMR (500 MHz, CDCl₃) δ 7.16 (d, J=8.0 Hz, 1H), 6.99 (m, 2H), 6.44 (t, J=7.5 Hz, 1H), 6.23 (s, 1H), 5.98 (dt, J=16.0 Hz, J=1.5 Hz, 1H), 4.17 (m, 2H), 3.73 (s, 3H), 3.37 (t, J=6.0 Hz, 2H), 2.77 (t, J=6.0 Hz, 2H), 1.89 (m, 2H). ¹³C NMR (125 MHz, CDCl₃) δ 169.9, 166.6, 147.1, 144.8, 132.6, 125.1, 122.9, 121.4, 113.8, 112.5, 51.8, 41.2, 40.3, 27.9, 20.9. HRMS [M-H]⁺ calculated for $C_{15}H_{19}N_2O_3$: 275.1396; found: 275.1396. HPLC-UV: 98.1%.

Compound 5 Characterization

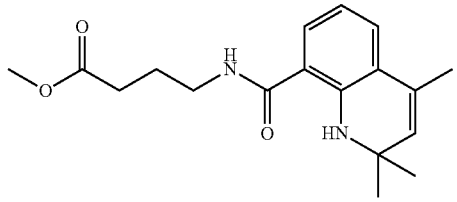

¹H NMR (500 MHz, CDCl₃) δ 7.14 (dd, J=8.0 Hz, J=0.5 Hz, 1H), 7.08 (dd, J=7.0 Hz, J=1.0 Hz, 1H), 6.46 (t, J=7.5 Hz, 1H), 6.36 (s, 1H), 5.34 (d, J=1.0 Hz, 1H), 3.67 (s, 3H), 3.43 (q, J1=7.0 Hz, J2=12.5 Hz, 2H), 2.43 (t, J=7.5 Hz, 2H), 1.96 (s, 3H), 1.96 (m, 2H), 1.31 (1, 6H). ¹³C NMR (125 MHz, CDCl₃) δ 174.2, 169.8, 145.9, 129.0, 127.65, 126.6, 126.3, 122.7, 114.1, 112.4, 51.9, 51.6, 39.3, 32.1, 31.8, 24.6, 19.2. HRMS [M-H]⁺ calculated for $C_{18}H_{25}N_2O_3$: 317.1865; found: 317.1859. HPLC-UV: 96.0%.

Compound 6 Characterization

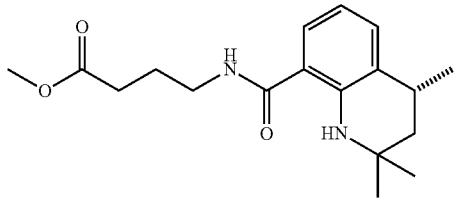

¹H NMR (500 MHz, CDCl₃) δ 7.76 (s, 1H), 7.21 (d, J=7.5 Hz, 1H), 7.16 (d, J=8.0 Hz, 1H), 6.49 (t, J=8.0 Hz, 1H), 6.32 (s, 1H), 3.67 (s, 3H), 3.43 (q, J1=6.5 Hz, J2=13.0 Hz, 2H), 2.90 (m, 1H), 2.42 (t, J=7.0 Hz, 2H), 1.93 (m, 2H), 1.71 (dd, J=13.0 Hz, J=5.5 Hz, 1H), 1.39 (t, J=15.5 Hz, 1H), 1.33 (d, J=6.5 Hz, 3H), 1.29 (s, 3H), 1.21 (s, 3H). ¹³C NMR (125 MHz, CDCl₃) δ 174.2, 170.3, 146.1, 129.7, 127.1, 125.2, 113.6, 113.2, 51.8, 48.9, 43.5, 39.2, 31.7, 28.9, 27.8, 24.7, 20.3. HRMS [M-H]⁺ calculated for $C_{18}H_{27}N_2O_3$: 319.2022; found: 319.2018. HPLC-UV: 96.7%.

Compound 7 Characterization

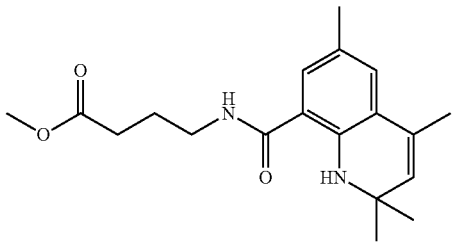

¹H NMR (500 MHz, CDCl₃) δ 6.96 (s, 1H), 6.92 (s,1H), 6.36 (s, 1H), 5.35 (s, 1H), 3.67 (s, 3H), 3.42 (q, J1=7.0 Hz, J2=13.0 Hz, 2H), 2.42 (t, J=7.0 Hz, 2H), 2.20 (s, 3H), 1.95 (s, 3H), 1.94 (m, 2H), 1.29 (s, 6H). ¹³C NMR (125 MHz, CDCl₃) δ 174.2, 169.8, 130.7, 129.4, 128.9, 127.7, 127.6, 126.2, 123.0, 112.6, 51.8, 51.5, 39.2, 31.7, 24.6, 20.7, 19.2. HRMS [M-H]⁺ calculated for $C_{19}H_{27}N_2O_3$: 329.1865; found: 329.1864. HPLC-UV: 98.7%.

Compound 8 Characterization

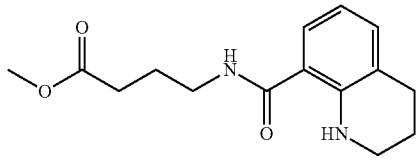 [SMILES: COC(=O)CCCNC(=O)c1cccc2c1NCCC2]

¹H NMR (500 MHz, CDCl₃) δ 7.63 (s, 1H), 7.12 (d, J=8.0 Hz, 1H), 6.97 (d, J=7.0 Hz, 1H), 6.43 (t, J=7.5 Hz, 1H), 6.30 (s, 1H), 3.66 (s, 3H), 3.42 (q, J=6.0 Hz, 2H), 3.36 (t, J=5.5 Hz, 2H), 2.75 (t, J=6.5 Hz, 2H), 2.42 (t, J=7.5 Hz, 2H), 1.92 (m 2H), 1.87 (m, 2H). ¹³C NMR (125 MHz, CDCl₃) δ 174.1, 170.1, 146.8, 132.2, 125.1, 122.7, 113.7, 113.4, 51.8, 41.2, 39.2, 31.7, 27.9, 24.7, 20.9. HRMS [M-H]⁺ calculated for $C_{15}H_2N_2O_3$: 277.1552; found: 277.1555. HPLC-UV: 98.1%.

Compound 9 Characterization

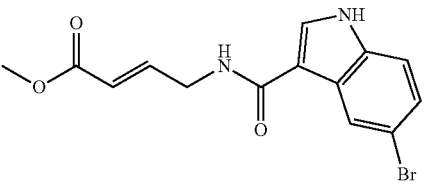 [SMILES: COC(=O)/C=C/CNC(=O)c1c[nH]c2ccc(Br)cc12]

¹H NMR (500 MHz, Acetone-d₆) δ 10.88 (s, 1H), 8.45 (m, 1H), 8.10 (d, J=3.0 Hz, 1H), 7.63 (s, 1H), 7.44 (dd, J=8.5 Hz, J=0.5 Hz, 1H), 7.28 (dd, J=8.5 Hz, J=2.0 Hz, 1H), 6.99 (dt, J=16.0 Hz, J=5.0 Hz, 1H), 5.98 (dt, J=16.0 Hz, J=1.5 Hz, 1H), 4.19-4.17 (m, 2H), 3.65 (s, 3H). ¹³C NMR (125 MHz, Acetone-d₆) δ 166.8, 165.0, 147.0, 136.1, 129.3, 129.1, 125.8, 124.6, 121.2, 114.6, 114.4, 114.3, 111.7, 51.5, 40.3. HRMS [M]⁻ calculated for $C_{14}H_{13}BrN_2O_3$: 335.0031; found: 335.0043. HPLC-UV: 99.9%.

Compound 10 Characterization

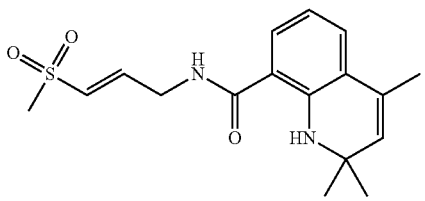 [SMILES: CC1=CC(C)(C)Nc2c(C(=O)NC/C=C/S(C)(=O)=O)cccc21]

¹H NMR (500 MHz, CDCl₃) δ 7.99 (s, 1H), 7.18 (d, J=8.0 Hz, 1H), 7.13 (d, J=7.5 Hz, 1H), 7.01 (dt, J=15.0 Hz, J=4.0 Hz, 1H), 6.53 (d, J=15.0 Hz, 1H), 6.49 (t, J=8.0 Hz, 1H), 6.31 (t, J=5.0 Hz, 1H), 5.36 (s, 1H), 4.27 (m, 2H), 2.95 (s, 3H), 1.97 (s, 3H), 1.32 (s, 6H). ¹³C NMR (125 MHz, CDCl₃) δ 169.5, 145.1, 144.6, 129.7, 129.0, 127.4, 127.1, 126.1, 122.8, 114.1, 110.8, 51.6, 42.8, 39.4, 32.1, 19.0. HRMS [M-H]⁺ calculated for $C_{17}H_{23}N_2O_3$: 335.1429; found: 335.1429. HPLC-UV: 97.2%.

Compound 11 Characterization

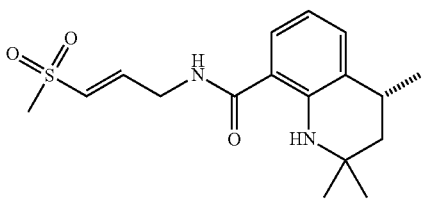 [SMILES: C[C@@H]1CC(C)(C)Nc2c(C(=O)NC/C=C/S(C)(=O)=O)cccc21]

¹H NMR (500 MHz, CDCl₃) δ 7.78 (s, 1H), 7.27 (d, J=7.5 Hz, 1H), 7.21 (d, J=8.0 Hz, 1H), 7.00 (dt, J=15.0 Hz, J=4.25 Hz, 1H), 6.52 (d, J=15.0 Hz, 1H), 6.52 (t, J=7.5 Hz, 1H), 6.35 (t, J=4.75 Hz, 1H), 4.25 (m, 2H), 2.93 (s, 3H), 1.75 (dd, J=13 Hz, J=5.0 Hz, 1H), 1.51 (s, 1H), 1.40 (t, J=13 Hz, 1H), 1.35 (d, J=6.5 Hz, 3H), 1.29 (s, 3H), 1.22 (s, 3H). ¹³C NMR (125 MHz, CDCl₃) δ 170.0, 146.2, 144.7, 130.2, 129.7, 127.5, 126.1, 125.1, 113.8, 43.2, 42.7, 39.50, 31.4, 28.9, 27.7, 20.2. HRMS [M-H]⁺ calculated for $C_{17}H_{25}N_2O_3S$: 337.1586; found: 337.1579. HPLC-UV: 99.9%.

Compound 12 Characterization

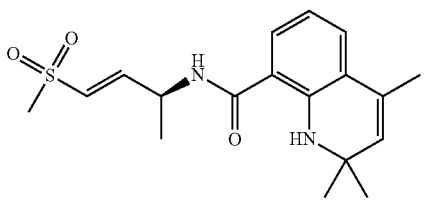 [SMILES: CC1=CC(C)(C)Nc2c(C(=O)N[C@@H](C)/C=C/S(C)(=O)=O)cccc21]

¹H NMR (500 MHz, CDCl₃) δ 7.96 (s, 1H), 7.17 (d, J=8.0 Hz, 1H), 7.11 (d, J=7.0 Hz, 1H), 6.95 (dd, J=15.0 Hz, J=4.5 Hz, 1H), 6.50 (d, J=15.5 Hz, 1H), 6.47 (t, J=8.0 Hz, 1H), 6.05 (d, J=7.5 Hz, 1H), 5.35 (s, 1H), 4.93 (m, 1H), 2.94 (s, 3H), 1.97 (s, 3H), 1.42 (d, J=7.5 Hz, 3H), 1.32 (s, 3H), 1.31 (s, 3H). ¹³C NMR (125 MHz, CDCl₃) δ 169.0, 148.8, 146.3, 129.1, 129.0, 127.5, 127.1, 126.2, 122.8, 114.1, 111.1, 51.7, 45.4, 42.9, 32.2, 19.9, 19.1. HRMS [M-H]⁺ calculated for $C_{18}H_{25}N_2O_3S$: 349.1586; found: 349.1584. HPLC-UV: 99.1%.

Compound 13 Characterization

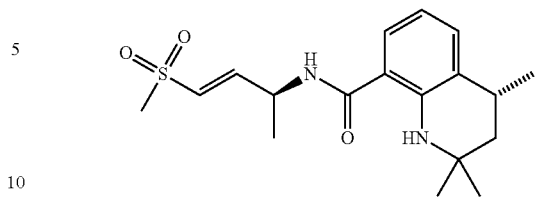

¹H NMR (500 MHz, CDCl₃) δ 7.73 (s, 1H), 7.25 (d, J=8.0 Hz, 1H), 7.20 (dd, J=7.5 Hz, J=3.0 Hz, 1H), 6.94 (dt, J=15.0 Hz, J=5.0 Hz, 1H), 6.52-6.48 (m, 2H), 6.08 (t, J=7.0 Hz, 1H), 4.93 (m, 1H), 2.94 (d, J=5.5 Hz, 3H), 1.74 (dd, J=12.5 Hz, J=5.0 Hz, 1H), 1.41 (m, 3H), 1.34 (dd, J=7.0 Hz, J=2.0 Hz, 3H), 1.22 (d, J=5.5, 3H). ¹³C NMR (125 MHz, CDCl₃) δ 169.5, 148.8, 130.3, 129.0, 127.5, 125.2, 113.7, 111.9, 49.0, 45.4, 43.4, 42.9, 31.1, 29.0, 27.8, 20.3, 19.8. HRMS [M-H]⁺ calculated for $C_{18}H_{27}N_2O_3S$: 351.1742; found: 351.1735. HPLC-UV: 97.0%.

Compound 14 Characterization

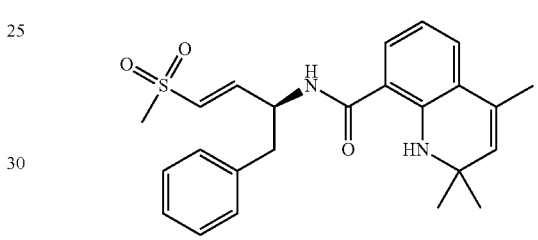

¹H NMR (500 MHz, CDCl₃) δ 7.91 (s, 1H), 7.34 (t, J=7.5 Hz, 2H), 7.29 (t, J=7.5 Hz, 1H), 7.21 (d, J=7.0 Hz, 2H), 7.10 (dd, J=7.5 Hz, J=1.0 Hz, 1H), 7.02-6.97 (m, 2H), 6.44 (t, J=8.0 Hz, 1H), 6.39 (dd, J=15.0 Hz, J=1.5 Hz, 1H), 6.07 (d, J=7.5 Hz, 1H), 5.14 (m, 1H), 3.05 (d, J=7.0 Hz, 2H), 2.88 (s, 3H), 1.95 (d, J=15.0 Hz, 3H), 1.30 (s, 6H). ¹³C NMR (125 MHz, CDCl₃) δ 168.9, 147.0, 146.1, 135.5, 129.8, 129.3, 129.0, 128.9, 127.4, 127.0, 125.9, 122.7, 114.0, 110.9, 51.6, 50.2, 42.8, 40.0, 32.1, 19.0. HRMS [M-Cl]⁻ calculated for $C_{24}H_{28}ClN_2O_3S$: 459.1509; found: 459.1517. HPLC-UV: 97.8%.

Compound 15 Characterization

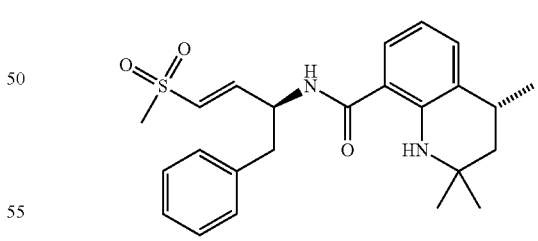

¹H NMR (500 MHz, CDCl₃) δ 7.70 (d J=30.0 Hz, 1H), 7.33 (m, 2H), 7.28 (m 1H), 7.21 (m, 2H), 7.05 (dd, J=15.5 Hz, J=3.0 Hz, 1H), 6.98 (dd, J=15.0 Hz, J=4.5 Hz, 1H), 6.48 (td, J=7.5 Hz, J=1.5 Hz, 1H), 6.39 (m, 1H), 6.12 (t, J=7.5 Hz, 1H), 5.14 (m, 1H), 3.05 (m, 2H), 2.87 (d, J=2.5 Hz, 3H), 1.73 (dd, J=12.5 Hz, J=5.0 Hz, 1H), 1.38 (t, J=12.5 Hz, 1H), 1.34 (d, J=7.0 Hz, 3H), 1.27 (d, J=6.0 Hz, 3H), 1.20 (s, 3H). ¹³C NMR (125 MHz, CDCl₃) δ 169.4, 147.2, 146.5, 135.6, 130.2, 129.9, 129.4, 129.0, 127.5, 125.1, 113.7, 111.7, 50.4, 49.0, 43.3, 42.9, 40.1, 31.6, 29.0, 27.8, 20.3. HRMS [M-Cl]⁻ calculated for $C_{24}H_{30}ClN_2O_3S$: 461.1666; found: 461.1668. HPLC-UV: 98.0%.

Compound 16 Characterization

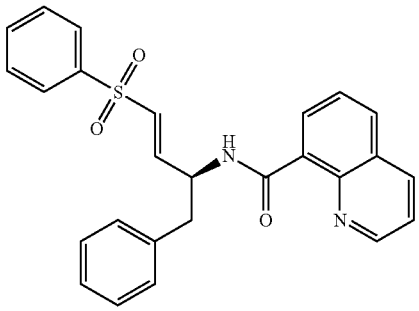 [SMILES: O=C(N[C@H](/C=C/S(=O)(=O)c1ccccc1)Cc1ccccc1)c1cccc2cccnc12]

¹H NMR (500 MHz, CDCl₃) δ 11.67(d, J=8.5 Hz, 1H), 8.78 (dd, J=7.0 Hz, J=1.5 Hz, 1H), 8.73 (dd, J=4.0 Hz, J=2.0 Hz, 1H), 8.29 (dd, J=8.5 Hz, J=2.0 Hz, 1H), 7.98 (dd, J=8.5 Hz, J=1.5 Hz, 1H), 7.81 (m, 2H), 7.66 (t, J=7.75 Hz, 1H), 7.59 (t, J=7.0 Hz, 1H), 7.51-7.48 (m, 3H), 7.27-7.23 (m, 5H), 7.18 (dd, J=15.0 Hz, J=5.0 Hz, 1H), 6.44 (dd, J=15.0 Hz, J=1.5 Hz, 1H), 5.45 (m, 1H), 3.22-3.11 (m, 2H). ¹³C NMR (125 MHz, CDCl₃) δ 165.2, 149.2, 146.5, 145.4, 140.2, 137.8, 136.2, 134.0, 133.3, 132.3, 130.5, 129.7, 129.2, 128.4, 127.8, 127.6, 126.9, 126.5, 121.0, 51.2, 40.5. HRMS [M-Cl]⁻ calculated for $C_{26}H_{22}ClN_2O_3S$: 477.1040; found: 477.1039. HPLC-UV: 97.6%.

Compound 17 Characterization

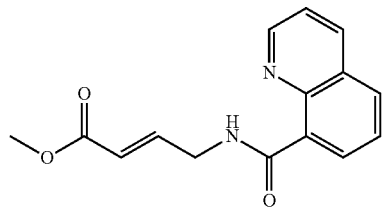 [SMILES: COC(=O)/C=C/CNC(=O)c1cccc2cccnc12]

¹H NMR (500 MHz, CDCl₃) δ 11.61 (s, 1H), 8.94 (dd, J=4.5 Hz, J=1.5 Hz, 1H), 8.87 (dd, J=7.5 Hz, J=1.5 Hz, 1H), 8.30 (dd, J=8.5 Hz, J=1.5 Hz, 1H), 7.99 (dd, J=8.0 Hz, J=1.5 Hz, 1H), 7.69 (t, J=8.0 Hz, 1H), 7.51 (dd, J=8.5 Hz, J=4.5 Hz, 1H), 7.15 (dt, J=15.5 Hz, J=4.5 Hz, 1H), 6.10 (dt, J=16.0 Hz, J=2.0 Hz, 1H), 4.43 (m, 2H), 3.72 (s, 3H). ¹³C NMR (125 MHz, CDCl₃) δ 166.8, 166.1, 149.5, 145.7, 145.4, 138.0, 134.2, 132.3, 128.6, 128.3, 126.7, 121.1, 120.9, 51.7, 40.6. HRMS [M-H]⁺ calculated for $C_{15}H_{15}N_2O_3$: 271.1083; found: 271.1081. HPLC-UV: 98.7%.

Compound 18 Characterization

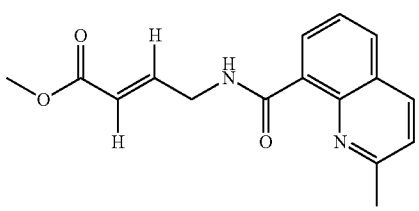 [SMILES: COC(=O)/C=C/CNC(=O)c1cccc2ccc(C)nc12]

¹H NMR (500 MHz, CDCl₃) δ 11.88 (s, 1H), 8.82 (d, J=7.0 Hz, 1H), 8.17 (d, J=8.5 Hz, 1H), 7.93 (d, J=8.0 Hz, 1H), 7.62 (t, J=8.0 Hz, 1H), 7.37 (d, J=8.5 Hz, 1H), 7.18 (dt, J=15.5 Hz, J=4.5 Hz, 1H), 6.18 (d, J=16.0 Hz, 1H), 4.45 (m, 2H), 3.73 (s, 3H), 2.78 (s, 3H). ¹³C NMR (125 MHz, CDCl₃) 67 166.7, 164.8, 145.3, 145.1, 137.8, 133.89, 131.9, 125.6, 121.8, 120.5, 118.0, 51.6, 40.4, 29.7. HRMS [M-H]⁺ calculated for $C_{16}H_{17}N_2O_3$: 285.1239; found: 285.1244. HPLC-UV: 99.8%.

Compound 19 Characterization

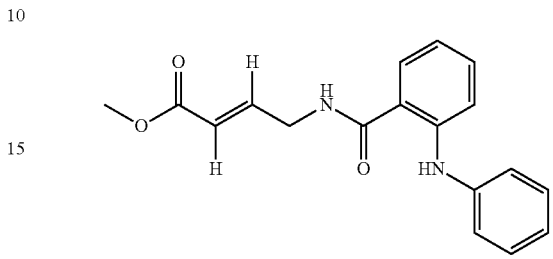

¹H NMR (500 MHz, CDCl₃) δ 9.28 (s, 1H), 7.46 (dd, J=7.5 Hz, J=1.0 Hz, 1H), 7.34 (t, J=7.5, 1H), 7.29 (m, 2H), 7.28 (m, 1H), 7.19 (d, J=7.5 Hz, 2H), 7.02 (t, J=7.0 Hz, 1H), 6.99 (dt, J=16.0 Hz, J=5.0 Hz, 1H), 6.77 (t, J=7.5 Hz, 1H), 6.42 (s, 1H), 6.00 (dt, J=15.5 Hz, J=1.5 Hz, 1H), 4.21 (m, 2H), 3.73 (s, 3H). ¹³C NMR (125 MHz, CDCl₃) δ 169.5, 166.5, 145.9, 144.2, 141.4, 132.7, 129.4, 127.5, 122.7, 121.7, 121.1, 118.0, 117.4, 115.6, 51.8, 40.5. HRMS [M-H]⁺ calculated for $C_{18}H_{19}N_2O_3$: 311.1396; found: 311.1398. HPLC-UV: 99.3%.

Compound 20 Characterization

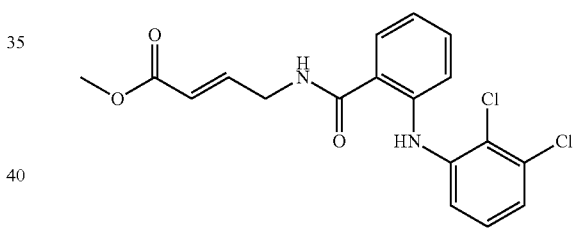

¹H NMR (500 MHz, CDCl₃) δ 9.23 (s, 1H), 7.50 (d, J=8.0 Hz, 1H), 7.34 (t, J=8.5 Hz, 1H), 7.30 (d, J=7.5 Hz, 1H), 7.18 (d, J=8.5 Hz, 2H), 7.03 (t, J=7.5 Hz, 1H), 6.99 (dt, J=15.0 Hz, J=4.5 Hz, 1H), 6.80 (t, J=7.5 Hz, 1H), 6.70 (s, 1H), 6.51 (d, J=15.0 Hz, 1H), 4.29 (m, 2H), 2.92 (s, 3H). ¹³C NMR (125 MHz, CDCl₃) δ 169.5, 145.9, 144.54, 141.4, 133.0, 130.0, 129.5, 127.7, 122.9, 121.1, 118.3, 117.1, 115.9, 42.9, 39.7. HRMS [M-H]⁺ calculated for $C_{18}H_{17}Cl_2N_2O_3$: 379.0616; found: 379.0609. HPLC-UV: 95.5%.

Compound 21 Characterization

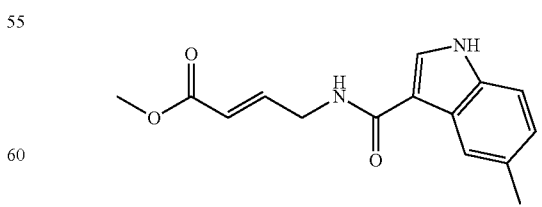

¹H NMR (500 MHz, CDCl₃) δ 8.83 (s, 1H), 7.74 (d, J=9.5 Hz, 2H), 7.32 (d, J=8.0 Hz, 1H), 7.09 (d, J=8.5 Hz, 1H), 7.05 (dt, J=15.5 Hz, J=5.0 Hz, 1H), 6.21 (s, 1H), 6.03 (dd, J=15.5 Hz, J=2.0 Hz, 1H), 4.30 (m, 2H), 3.72 (s, 3H), 2.48 (s, 3H).

$^{13}$C NMR (125 MHz, CDCl$_3$) δ 166.7, 165.5, 145.1, 134.7, 131.4, 128.3, 124.9, 124.8, 121.4, 119.7, 111.7, 111.4, 51.8, 40.3, 21.7. HRMS [M-H]$^+$ calculated for C$_{15}$H$_{17}$N$_2$O$_3$: 273.1239; found: 273.1245. HPLC-UV: 99.9%.

Compound 22 Characterization

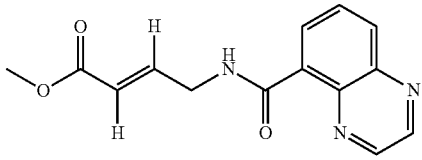 [SMILES: COC(=O)/C=C/CNC(=O)c1cccc2nccnc12]

$^1$H NMR (500 MHz, CDCl$_3$) δ 10.72 (s, 1H), 8.99 (d, J=1.5 Hz, 1H), 8.91 (dd, J=7.5 Hz, J=1.5 Hz, 1H), 8.88 (d, J=1.5 Hz, 1H), 8.30 (dd, J=8.5 Hz, J=1.5 Hz, 1H), 7.93 (t, J=8.0 Hz, 1H), 7.12 (dt, J=15.5 Hz, J=4.75 Hz, 1H), 6.07 (dt, J=16.0 Hz, J=1.75 Hz, 1H), 4.44-4.41 (m, 2H), 3.72 (s, 3H). $^{13}$C NMR (125 MHz, CDCl$_3$) δ 166.7, 164.9, 145.0, 144.0, 143.0, 143.2, 140.8, 134.6, 134.1, 130.4, 128.7, 121.3, 51.8, 40.3. HRMS [M-H]$^+$ calculated for C$_{14}$H$_{14}$N$_3$O$_3$: 272.1035; found: 272.1044. HPLC-UV: 99.8%.

Compound 23 Characterization

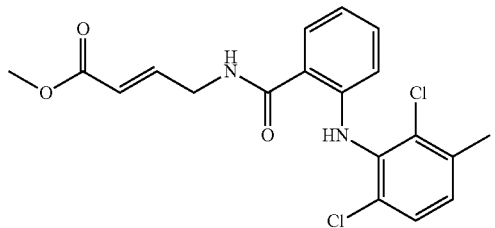

$^1$H NMR (500 MHz, CDCl$_3$) δ 9.27 (s, 1H), 7.49 (dd, J=8.0 Hz, J=1.5 Hz, 1H), 7.27 (d, J=8.0 Hz, 1H), 7.23 (t, J=7.0 Hz, 1H), 7.06 (d, J=8.0 Hz, 1H), 7.02 (dt, J=15.5 Hz, J=5.0 Hz, 1H), 6.77 (t, J=7.0 Hz, 1H), 6.54 (s, 1H), 6.38 (d, J=8.0 Hz, 1H), 6.03 (dt, J=15.5 Hz, J=1.5 Hz, 1H), 4.25 (m, 2H), 3.73 (s, 3H), 2.39 (s, 3H). $^{13}$C NMR (125 MHz, CDCl$_3$) δ 169.5, 166.8, 145.9, 144.4, 136.0, 135.2, 133.8, 132.0, 130.7, 127.0, 127.3, 127.4, 121.9, 118.0, 116.7, 115.0, 51.8, 40.4, 20.7. HRMS [M-H]$^+$ calculated for C$_{19}$H$_{19}$Cl$_2$N$_2$O$_3$: 393.0773; found: 393.0773. HPLC-UV: 97.0%.

Compound 24 Characterization

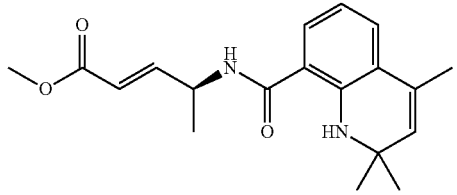

$^1$H NMR (500 MHz, CDCl$_3$) δ 7.95 (s, 1H), 7.15 (d, J=8.0 Hz, 1H), 7.10 (d, J=7.0 Hz, 1H), 6.98 (dd, J=15.5 Hz, J=5.0 Hz, 1H), 6.46 (t, J=7.5 Hz, 1H), 5.97 (s, 1H), 5.96 (dd, J=15.5 Hz, J=1.5 Hz, 1H), 5.35 (s, 1H), 4.87 (m, 1H), 3.73 (s, 3H), 1.96 (s, 3H), 1.38 (d, J=7.0 Hz, 3H), 1.32 (s, 3H), 1.31 (s, 3H). $^{13}$C NMR (125 MHz, CDCl$_3$) δ 168.9, 166.8, 149.3, 146.2, 129.1, 127.5, 126.9, 126.2, 122.8, 120.2, 114.0, 111.7, 51.8, 51.7, 45.7, 32.2, 32.1, 20.2, 19.2. HRMS [M-H]$^+$ calculated for C$_{19}$H$_{25}$N$_2$O$_3$: 329.1865; found: 329.1861. HPLC-UV: 95.3%.

Compound 25 Characterization

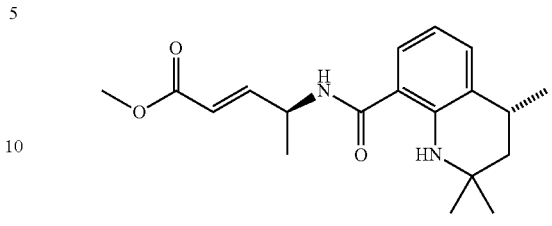

$^1$H NMR (500 MHz, CDCl$_3$) δ 7.72 (s, 1H), 7.24 (d, J=7.5 Hz, 1H), 7.18 (dd, J=7.5 Hz, J=4.5 Hz, 1H), 6.97 (dd, J=16.0 Hz, J=4.5 Hz, 1H), 6.50 (m, 1H), 5.95 (m, 2H), 4.86 (m, 2H), 3.73 (s, 3H), 2.91 (m, 1H), 1.72 (dd, J=12.5 Hz, J=4.5 Hz, 1H), 1.37 (m, 4H), 1.33 (dd, J=7.0 Hz, J=1.5 Hz, 3H), 1.28 (d, J=4.0 Hz, 3H), 1.21 (d, J=4.0 Hz, 3H). $^{13}$C NMR (125 MHz, CDCl$_3$) 67 169.4, 166.8, 149.3, 146.3, 130.0, 127.3, 125.1, 120.1, 113.6, 112.3, 51.81, 49.0, 45.7, 43.4, 31.6, 29.1, 27.8, 20.3, 20.1. HRMS [M-H]$^+$ calculated for C$_{19}$H$_{27}$N$_2$O$_3$: 331.2022; found: 331.2016. HPLC-UV: 99.1%.

Compound 26 Characterization

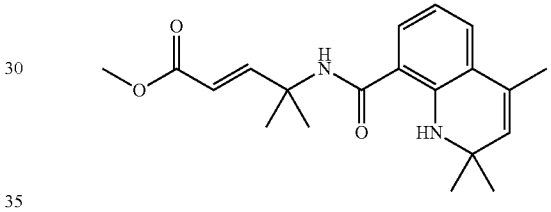

$^1$H NMR (500 MHz, CDCl$_3$) δ 7.75 (s, 1H), 7.15 (d, J=15.5 Hz, 1H), 7.13 (d, J=8.0 Hz, 1H), 7.08 (d, J=7.0 Hz, 1H), 6.45 (t, J=7.5 Hz, 1H), 5.99 (s, 1H), 5.90 (d, J=16.0 Hz, 1H), 5.33 (s, 1H), 3.73 (s, 3H), 1.96 (s, 3H), 1.54 (s, 6H), 1.30 (s, 6H). $^{13}$C NMR (125 MHz, CDCl$_3$) δ 169.2, 167.2, 153.8, 145.9, 129.2, 127.5, 126.7, 126.3, 122.8, 118.3, 114.0, 112.8, 53.9, 51.7, 32.1, 27.6, 19.2. HRMS [M-H]$^+$ calculated for C$_{20}$H$_{27}$N$_2$O$_3$: 343.2022; found: 343.2026. HPLC-UV: 99.8%.

Compound 27 Characterization

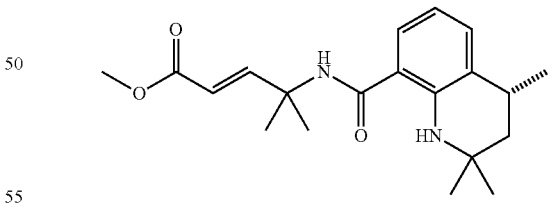

$^1$H NMR (500 MHz, CDCl$_3$) δ 7.48 (s, 1H), 7.22 (d, J=7.5 Hz, 1H), 7.51 (d, J=8.0 Hz, 1H), 7.49 (d, J=16.5 Hz, 1H), 6.49 (t, J=7.75 Hz, 1H), 5.99 (s, 1H), 5.91 (d, J=16.0 Hz, 1H), 3.72 (s, 3H), 2.94-2.86 (m, 1H), 1.72 (dd, J=12.5 Hz, J=4.5 Hz, 1H), 1.54 (s, 3H), 1.53 (s, 3H), 1.38 (t, J=12.75 Hz, 1H), 1.33 (d, J=6.5 Hz, 3H), 1.27 (s, 3H), 1.20 (s, 3H). $^{13}$C NMR (125 MHz, CDCl$_3$) δ 169.7, 167.2, 153.8, 146.0, 129.8, 127.3, 125.3, 118.3, 113.8, 113.6, 53.9, 51.7, 49.0, 43.6, 31.6, 28.9, 27.8, 27.7, 27.5, 20.4. HRMS [M-H]$^+$ calculated for C$_{20}$H$_{29}$N$_2$O$_3$: 345.2178; found: 345.2175. HPLC-UV: 97.1%.

Compound 28 Characterization

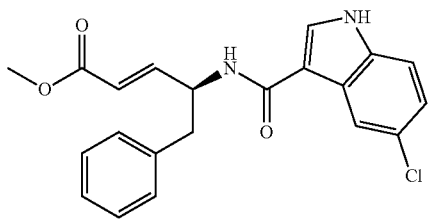 [SMILES: COC(=O)/C=C/[C@H](Cc1ccccc1)NC(=O)c1c[nH]c2ccc(Cl)cc12]

$^{1}$H NMR (500 MHz, CDCl$_3$) δ 9.22 (s, 1H), 7.52 (d, J=2.5 Hz, 1H), 7.38 (s, 1H), 7.28 (t, J=7.0 Hz, 1H), 7.22 (t, J=7.5 Hz, 3H), 7.05 (dd, J=15.5 Hz, J=5.0 Hz, 1H), 6.85 (dd, J=9.0 Hz, 1H), 6.08 (d, J=8.0 Hz, 1H), 5.93 (d, J=15.5 Hz, 1H), 5.20 (m, 1H), 3.78 (s, 3H), 3.05 (d, J=7.0 Hz, 2H). $^{13}$C NMR (125 MHz, CDCl$_3$) δ 166.9, 165.3, 155.6, 148.2, 136.4, 131.3, 129.4, 128.8, 127.8, 127.1, 125.8, 121.0, 113.5, 112.8, 111.1, 102.0, 55.9, 51.8, 50.8, 40.4. HRMS [M]$^-$ calculated for C$_{21}$H$_{19}$ClN$_2$O$_3$: 381.1084; found: 381.1084. HPLC-UV: 99.9%.

Compound 29 Characterization

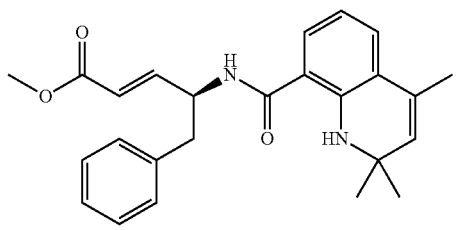

$^{1}$H NMR (500 MHz, CDCl$_3$) δ 7.87 (s, 1H), 7.32 (t, J=7.0 Hz, 2H), 7.26 (t, J=3.75 Hz, 1H), 7.21 (d, J=7.0 Hz, 2H), 7.08 (d, J=7.0 Hz, 1H), 7.02 (dd, J=15.5 Hz, J=5.0 Hz, 1H), 6.98 (d, J=9.0 Hz, 1H), 6.42 (t, J=8.0 Hz, 1H), 5.95 (d, J=8.0 Hz, 1H), 5.89 (dd, J=15.5 Hz, J=1.5 Hz, 1H), 5.34 (s, 1H), 5.09 (m, 1H), 3.72 (s, 3H), 3.07-2.98 (m, 2H), 1.95 (d, J=1.5 Hz, 3H), 1.30 (s, 6H). $^{13}$C NMR (125 MHz, CDCl$_3$) δ 168.9, 166.6, 147.6, 146.0, 136.2, 129.4, 129.1, 128.8, 127.5, 127.2, 126.9, 126.0, 122.8, 121.1, 114.1, 111.8, 51.8, 51.7, 50.7, 40.5, 32.1, 29.8, 19.1. HRMS [M]$^-$ calculated for C$_{25}$H$_{28}$N$_2$O$_3$: 403.2022; found: 403.2022. HPLC-UV: 95.0%.

Compound 30 Characterization

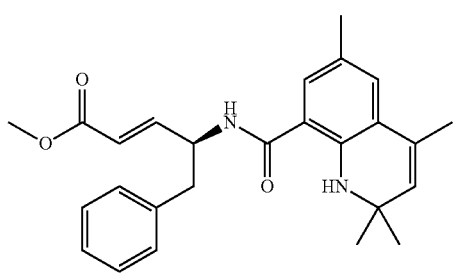

$^{1}$H NMR (500 MHz, CDCl$_3$) δ 7.33 (t, J=7.5 Hz, 2H), 7.26 (t, J=7.25 Hz, 1H), 7.21 (d, J=7.0 Hz, 2H), 7.02 (dd, J=15.5 Hz, J=5.0 Hz, 1H), 6.92 (s, 1H), 6.77 (s, 1H), 5.93 (d, J=8.0 Hz, 1H), 5.89 (dd, J=15.5 Hz, J=1.5 Hz, 1H), 5.35 (s, 1H), 5.09 (m, 1H), 3.72 (s, 3H), 3.07-2.99 (m, 2H), 2.18 (s, 3H), 1.95 (d, J=0.5 Hz, 3H), 1.28 (s, 6H). $^{13}$C NMR (125 MHz, CDCl$_3$) δ 168.8, 166.6, 147.6, 136.2, 129.6, 129.5, 128.8, 128.1, 127.6, 127.2, 126.0, 121.1, 51.8, 50.8, 40.5, 32.2, 31.6, 29.8, 20.7, 19.2. HRMS [M]$^-$ calculated for C$_{26}$H$_{30}$N$_2$O$_3$: 417.2178; found: 417.2181. HPLC-UV: 96.8%.

Compound 31 Characterization

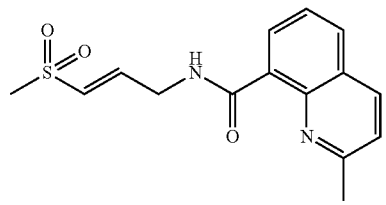 [SMILES: Cc1ccc2cccc(C(=O)NC/C=C/S(C)(=O)=O)c2n1]

$^{1}$H NMR (500 MHz, CDCl$_3$) δ 11.95 (s, 1H), 8.81 (d, J=7.0 Hz, 1H), 8.20 (d, J=8.5 Hz, 1H), 7.97 (d, J=8.0 Hz, 1H), 7.64 (t, J=7.5 Hz, 1H), 7.40 (d, J=8.5 Hz, 1H), 7.15 (dt, J=15.5 Hz, J=4.0 Hz, 1H), 6.68 (dt, J=15.5 Hz, J=1.5 Hz, 1H), 4.52 (m, 2H), 2.94 (s, 3H), 2.80 (s, 3H). $^{13}$C NMR (125 MHz, CDCl$_3$) δ 166.5, 159.0, 145.5, 140.1, 138.2, 134.1, 132.3, 129.6, 126.9, 125.8, 122.1, 43.0, 39.9, 25.7. HRMS [M-H]$^+$ calculated for C$_{15}$H$_{17}$N$_2$O$_3$S: 305.0960; found: 305.0960. HPLC-UV: 95.0%.

Compound 32 Characterization

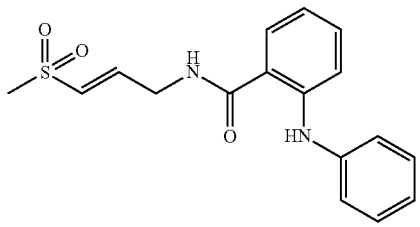 [SMILES: CS(=O)(=O)/C=C/CNC(=O)c1ccccc1Nc1ccccc1]

$^{1}$H NMR (500 MHz, CDCl$_3$) δ 9.47 (s, 1H), 7.53 (d, J=7.5 Hz, 1H), 7.36 (m, 2H), 7.32 (dd, J=8.0 Hz, J=1.5 Hz, 1H), 7.09 (t, J=8.0 Hz, 1H), 7.05 (dd, J=8.0 Hz, J=1.0 Hz, 1H), 6.97 (dt, J=15.5 Hz, J=5.0 Hz, 1H), 6.91 (m, 1H), 6.49 (s, 1H), 5.98 (d, J=16.0 Hz, 1H), 4.23 (m, 2H), 3.72 (s, 3H). $^{13}$C NMR (125 MHz, CDCl$_3$) δ 168.9, 166.4, 143.9, 143.4, 140.7, 133.8, 132.5, 127.8, 127.1, 123.3, 122.9, 121.8, 120.1, 117.3, 116.4, 51.8, 40.5. HRMS [M-H]$^+$ calculated for C$_{17}$H$_{19}$N$_2$O$_3$S: 331.1116; found: 331.1123. HPLC-UV: 95.6%.

Compound 33 Characterization

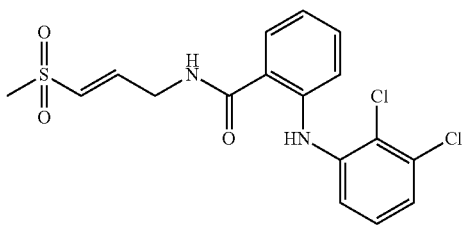 [SMILES: CS(=O)(=O)/C=C/CNC(=O)c1ccccc1Nc1cccc(Cl)c1Cl]

$^{1}$H NMR (500 MHz, CDCl$_3$) δ 9.48 (s, 1H), 7.57 (d, J=8.0 Hz, 1H), 7.38 (d, J=3.5 Hz, 2H), 7.32 (dd, J=8.0 Hz, J=1.5 Hz, 1H), 7.10 (t, J=8.0 Hz, 1H), 7.07 (dt, J=8.0 Hz, J=1.5 Hz, 1H), 6.98 (dt, J=15.0 Hz, J=4.0 Hz, 1H), 6.94 (m, 1H), 6.75

(t, J=5.5 Hz, 1H), 6.51 (dt, J=15.5 Hz, J=1.5 Hz, 1H), 4.31 (m, 2H), 2.92 (s, 3H). $^{13}$C NMR (125 MHz, CDCl$_3$) δ 169.1, 144.4, 143.5, 140.6, 133.9, 132.8, 130.0, 127.9, 127.2, 123.2, 123.0, 120.3, 119.7, 117.5, 116.4, 42.9, 39.7. HRMS [M-H]$^+$ calculated for C$_{17}$H$_{17}$Cl$_2$N$_2$O$_3$S: 399.0337; found: 399.0336. HPLC-UV: 99.9%.

Compound 34 Characterization

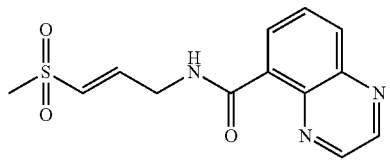 [SMILES: CS(=O)(=O)/C=C/CNC(=O)c1cccc2nccnc12]

$^1$H NMR (500 MHz, CDCl$_3$) δ 10.80 (s, 1H), 9.00 (d, J=1.5 Hz, 1H), 8.89 (d, J=2.0 Hz, 1H), 8.87 (dd, J=7.0 Hz, J=1.5 Hz, 1H), 8.32 (dd, J=8.0 Hz, J=1.5 Hz, 1H), 7.94 (t, J=8.0 Hz, 1H), 7.10 (dt, J=15.0 Hz, J=4.5 Hz, 1H), 6.59 (dt, J=15.0 Hz, J=2.0 Hz, 1H), 4.49 (m, 2H), 2.93 (s, 3H). $^{13}$C NMR (125 MHz, CDCl$_3$) δ 165.1, 145.1, 144.9, 143.6, 143.3, 140.2, 134.7, 134.2, 130.2, 129.8, 128.4, 42.9, 39.9. Mass [M-H]$^+$ for HRMS [M-H]$^+$ calculated for C$_{13}$H$_{14}$N$_3$O$_3$S: 292.0756; found: 292.0755. HPLC-UV: 99.9%.

Compound 35 Characterization

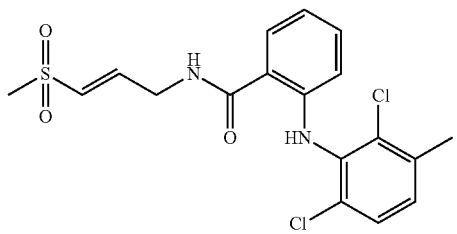

$^1$H NMR (500 MHz, CDCl$_3$) δ 9.25 (s, 1H), 7.52 (d, J=8.0 Hz, 1H), 7.28 (d, J=8.5 Hz, 1H), 7.25 (t, J=8.5 Hz, 1H), 7.07 (d, J=8.0 Hz, 1H), 7.01 (dt, J=15.5 Hz, J=4.5 Hz, 1H), 6.81 (t, J=7.5 Hz, 1H), 6.71 (t, J=5.5 Hz, 1H), 6.57 (d, J=15.0 Hz, 1H), 6.39 (d, J=8.5 Hz, 1H), 4.33 (s, 2H), 2.94 (s, 3H), 2.40 (s, 3H). $^{13}$C NMR (125 MHz, CDCl$_3$) δ 169.7, 145.8, 144.7, 136.5, 135.5, 133.4, 132.7, 130.3, 129.8, 128.0, 127.8, 127.5, 118.1, 116.2, 115.0, 42.9, 39.7, 20.7. HRMS [M-H]$^+$ calculated for C$_{18}$H$_{19}$Cl$_2$N$_2$O$_3$S: 413.0493; found: 413.0500. HPLC-UV: 99.2%.

Compound 36 Characterization

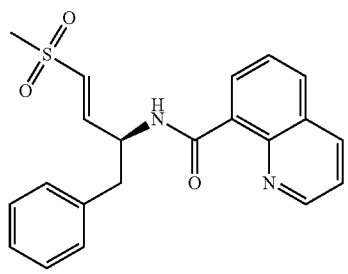 [SMILES: CS(=O)(=O)/C=C/[C@H](Cc1ccccc1)NC(=O)c1cccc2cccnc12]

$^1$H NMR (500 MHz, CDCl$_3$) δ 11.73 (d, J=8.0 Hz, 1H), 8.80 (m, 2H), 8.30 (dd, J=8.5 Hz, J=2.0 Hz, 1H), 7.99 (dd, J=8.0 Hz, J=1.0 Hz, 1H), 7.69 (t, J=7.5 Hz, 1H), 7.51 (dd, J=8.0 Hz, J=4.0 Hz, 1H), 7.31 (m, 3H), 7.26 (m, 1H), 7.12 (dd, J=15.0 Hz, J=4.5 Hz, 1H), 6.46 (dd, J=15.0 Hz, J=1.5 Hz, 1H), 5.43 (m, 1H), 3.22-3.13 (m, 2H), 2.86 (s, 3H). $^{13}$C NMR (125 MHz, CDCl$_3$) δ 165.5, 149.4, 148.0, 145.6, 138.0, 136.3, 134.2, 132.5, 129.8, 127.7, 128.6, 127.2, 126.7, 121.2, 51.5, 43.0, 40.4. HRMS [M-Cl]$^-$ calculated for C$_{23}$H$_2$OClN$_2$O$_3$S: 415.0883; found: 415.0879. HPLC-UV: 99.1%.

Compound 37 Characterization

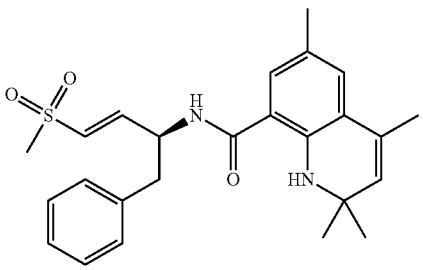 [SMILES: CC1=CC(C)(C)Nc2c(C(=O)N[C@H](/C=C/S(C)(=O)=O)Cc3ccccc3)cc(C)cc21]

$^1$H NMR (500 MHz, CDCl$_3$) δ 7.68 (s, 1H), 7.34 (t, J=7.5 Hz, 2H), 7.29 (t, J=7.5 Hz, 1H), 7.22 (d, J=7.0 Hz, 2H), 6.99 (dd, J=15.5 Hz, J=5.0 Hz, 1H), 6.94 (s, 1H), 6.80 (s, 1H), 6.40 (dd, J=15.5 Hz, J=1.5 Hz, 1H), 6.06 (d, J=8.0 Hz, 1H), 5.36 (s, 1H), 5.14 (m, 1H), 3.05 (d, J=6.0 Hz, 2H), 2.88 (s, 3H), 2.19 (s, 3H), 1.95 (d, J=1.0 Hz, 3H), 1.28 (s, 6H). $^{13}$C NMR (125 MHz, CDCl$_3$) δ 168.9, 147.2, 135.6, 129.9, 129.5, 129.4, 129.0, 128.3, 127.5, 125.9, 123.1, 111.2, 51.6, 50.3, 42.9, 40.2, 31.8, 20.7, 19.2. HRMS [M-Cl]-calculated for C$_{25}$H$_{30}$ClN$_2$O$_3$S: 473.1666; found: 473.1668. HPLC-UV: 98.4%.

Compound 38 Characterization

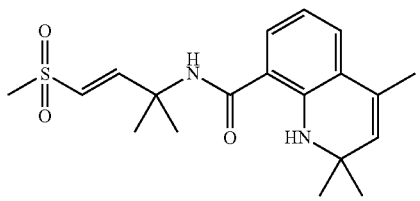

$^1$H NMR (500 MHz, CDCl$_3$) δ 7.75 (s, 1H), 7.12 (d, J=8.0 Hz, 1H), 7.10 (d, J=7.5 Hz, 1H), 7.05 (d, J=15.5 Hz, 1H), 6.47 (t, J=7.5 Hz, 1H), 6.42 (d, J=15.5 Hz, 1H), 6.04 (s, 1H), 5.34 (s, 1H), 2.97 (s, 3H), 1.96 (s, 3H), 1.56 (s, 6H), 1.30 (s, 6H). $^{13}$C NMR (125 MHz, CDCl$_3$) δ 169.2, 152.8, 146.0, 129.1, 127.5, 127.3, 127.0, 126.3, 122.8, 114.1, 112.1, 53.6, 51.7, 43.1, 32.2, 27.4, 19.1. HRMS [M-H]$^+$ calculated for C$_{19}$H$_{27}$N$_2$O$_3$S: 363.1742; found: 363.1742. HPLC-UV: 96.7%.

Compound 39 Characterization

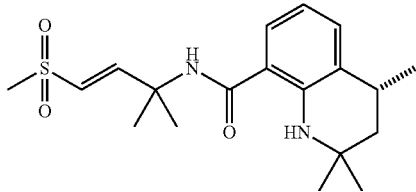

$^1$H NMR (500 MHz, CDCl$_3$) δ 7.45 (s, 1H), 7.24 (d, J=7.0 Hz, 1H), 7.15 (d, J=7.5 Hz, 1H), 7.04 (d, J=15.5 Hz, 1H), 6.51 (t, J=7.5 Hz, 1H), 6.43 (d, J=15.0 Hz, 1H), 6.03 (s, 1H), 2.98 (s, 3H), 2.90 (m, 1H), 1.73 (dd, J=12.5 Hz, J=5.0 Hz, 1H), 1.56 (s, 3H), 1.55 (s, 3H), 1.40 (m, 2H), 1.33 (d, J=7.0 Hz, 3H), 1.27 (s, 3H), 1.20 (s, 3H). $^{13}$C NMR (125 MHz, CDCl$_3$) δ 169.7, 152.8, 146.1, 130.1, 127.4, 125.2, 113.8, 113.2, 53.6, 49.0, 43.4, 43.2, 31.6, 29.0, 27.8, 27.5, 27.3, 20.3. HRMS [M-H]$^+$ calculated for C$_{19}$H$_{29}$N$_2$O$_3$S: 365.1899; found: 365.1897. HPLC-UV: 99.9%.

Compound 40 Characterization

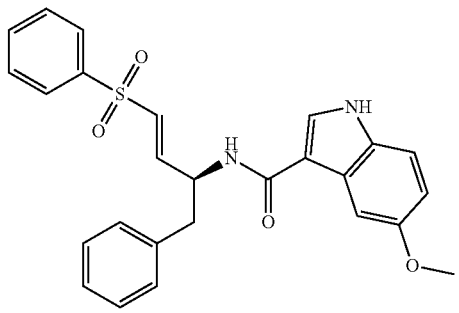 [SMILES: COc1ccc2[nH]cc(C(=O)N[C@H](/C=C/S(=O)(=O)c3ccccc3)Cc3ccccc3)c2c1]

$^1$H NMR (500 MHz, CDCl$_3$) δ 8.78 (s, 1H), 7.78 (d, J=7.5 Hz, 2H), 7.59 (m, 2H), 7.48 (t, J=8.0 Hz, 2H), 7.38 (d, J=2.0 Hz, 1H), 7.27-7.21 (m, 4H), 7.17 (m, 2H), 7.09 (dd, J=15.0 Hz, J=5.0 Hz, 1H), 6.87 (dd, J=8.5 Hz, J=2.0 Hz, 1H), 6.40 (dd, J=15.0, J=2.0 Hz, 1H), 6.07 (d, J=8.0 Hz, 1H), 5.28 (m, 1H), 3.77 (s,3H), 3.12-3.02 (m, 2H). $^{13}$C NMR (125 MHz, CDCl$_3$) δ 164.9, 155.5, 146.3, 139.7, 135.8, 133.5, 131.1, 130.7, 129.3, 128.7, 127.6, 127.5, 127.1, 125.6, 113.6, 112.6, 110.8, 101.9, 55.7, 50.1, 40.1, 29.7. HRMS [M]$^-$ calculated for C$_{26}$H$_{24}$N$_2$O$_4$S: 459.1378; found: 459.1380. HPLC-UV: 96.9%.

Compound 41 Characterization

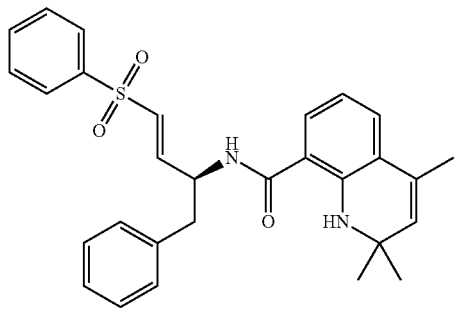 [SMILES: CC1=CC(C)(C)Nc2c(C(=O)N[C@H](/C=C/S(=O)(=O)c3ccccc3)Cc3ccccc3)cccc21]

$^1$H NMR (500 MHz, CDCl$_3$) δ 7.81 (m, 2H), 7.61 (t, J=7.5 Hz, 1H), 7.52 (t, J=7.5 Hz, 2H), 7.29 (t, J=7.5 Hz, 2H), 7.24 (m, 1H), 7.17 (m, 2H), 7.07 (m, 2H), 6.98 (d, J=7.5 Hz, 1H), 6.41 (t, J=8.0 Hz, 1H), 6.33 (dd, J=15.0 Hz, J=2.0 Hz, 1H), 6.01 (d, J=8.0 Hz, 1H), 5.32 (s, 1H), 5.14 (m, 1H), 3.02-3.00 (m, 2H), 1.94 (d, J=1.0 Hz, 3H), 1.28 (s, 3H), 1.24 (s, 3H). $^{13}$C NMR (125 MHz, CDCl$_3$) δ 168.8, 146.2, 145.7, 140.0, 135.6, 133.6, 130.9, 129.4, 129.1, 129.0, 127.8, 127.5, 127.4, 127.1, 126.0, 122.8, 114.0, 111.2, 51.7, 50.2, 40.2, 32.2, 32.1, 29.8, 19.1. HRMS [M]$^-$ calculated for C$_{29}$H$_{30}$N$_2$O$_3$S: 485.1899; found: 485.1895. HPLC-UV: 95.8%.

Compound 42 Characterization

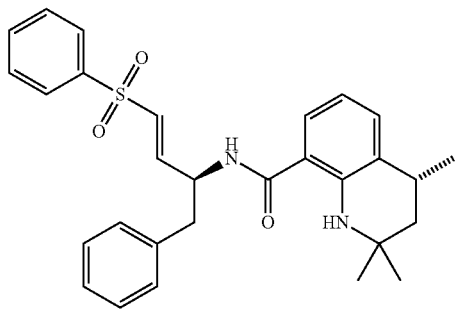 [SMILES: C[C@@H]1CC(C)(C)Nc2c(C(=O)N[C@H](/C=C/S(=O)(=O)c3ccccc3)Cc3ccccc3)cccc21]

$^1$H NMR (500 MHz, CDCl$_3$) δ 7.82 (d, J=8.5 Hz, 2H), 7.63-7.59 (m, 2H), 7.53-7.49 (m, 2H), 7.30-7.26 (m, 2H), 7.25-7.20 (m, 2H), 7.16 (t, J=7.0 Hz, 2H), 7.06-02 (m, 1H), 6.99 (dd, J=13.0 Hz, J=8.0 Hz, 1H), 6.44 (td, J=7.5 Hz, J=2.5 Hz, 1H), 6.33 (dt, J=15.5 Hz, J=2.0 Hz, 1H), 5.96 (t, J=9.0 Hz, 1H), 5.14 (m, 1H), 3.05-3.01 (m, 2H), 2.91-2.83 (m, 1H), 1.70 (dt, J=12.5 Hz, J=4.5 Hz, 1H), 1.36 (m, 1H), 1.32 (q, J=10.5 Hz, 3H), 1.25 (s, 3H), 1.17 (d, J=12.5 Hz, 3H). $^{13}$C NMR (125 MHz, CDCl$_3$) δ 169.2, 146.3, 145.8, 140.1, 135.6, 133.5, 130.8, 130.1, 129.4, 128.9, 127.8, 127.4, 125.0, 113.6, 111.7, 50.2, 49.0, 43.3, 40.2, 31.6, 29.8, 29.0, 27.7, 20.2. HRMS [M]$^-$ calculated for C$_{29}$H$_{32}$N$_2$O$_3$S: 487.2055; found: 487.2058. HPLC-UV: 99.9%.

Compound 43 Characterization

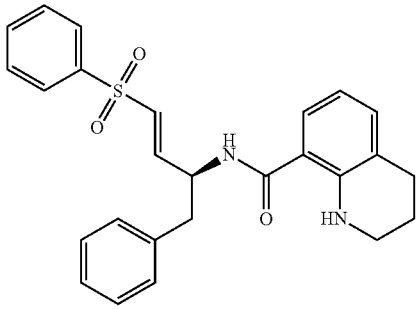 [SMILES: O=C(N[C@H](/C=C/S(=O)(=O)c1ccccc1)Cc1ccccc1)c1cccc2c1NCCC2]

$^1$H NMR (500 MHz, CDCl$_3$) δ 7.81 (m, 2H), 7.60 (t, J=7.5 Hz, 1H), 7.52 (t, J=7.5 Hz, 2H), 7.46 (s, 1H), 7.29 (t, J=7.5, 2H), 7.23 (t, J=7.5 Hz, 1H), 7.15 (d, J=6.5 Hz, 2H), 7.04 (dd, J=15.0 Hz, J=5.0 Hz, 1H), 6.97 (d, J=8.0 Hz, 2H), 6.38 (t, J=8.0 Hz, 1H), 6.34 (dd, J=15.0 Hz, J=1.5 Hz, 1H), 6.02 (d, J=8.0 Hz, 1H), 5.14 (m, 1H), 3.35-3.28 (m, 2H), 3.02 (d, J=7.0 Hz, 2H), 2.73 (t, J=6.5 Hz, 2H), 1.86 (m, 2H). $^{13}$C NMR (125 MHz, CDCl$_3$) δ 169.0, 146.9, 145.7, 139.9, 135.6, 133.4, 132.6, 130.7, 129.3, 129.2, 128.8, 127.6, 127.2, 124.9, 122.8, 113.7, 112.1, 50.1, 41.0, 40.1, 27.8, 20.6. HRMS [M]$^-$ calculated for C$_{26}$H$_{26}$N$_2$O$_3$S: 445.1586; found: 445.1578. HPLC-UV: 95.0%.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

The invention claimed is:

1. A composition comprising a compound configured to act as an inhibitor of the cysteine protease domain of Venezuelan equine encephalitis virus (VEEV's) non-structural protein 2 (nsp2), wherein the compound has the Formula (I):

Formula I or a stereoisomer, solvate and/or pharmaceutical acceptable salt thereof; wherein A is $C(O)OR_3$ or $S(O_2)R_3$;

$R_3$ is (C1-6)alkyl, (C3-7) cycloalkyl, (C3-7)cycloalkyl (C1-5)alkyl, optionally substituted aryl, or optionally substituted (C6-12)aralkyl;

$R_1$ and $R_2$ are independently selected from H, (C1-6)alkyl, (C3-7)cycloalkyl, (C3-7)cycloalkyl(C1-5)alkyl, optionally substituted aryl, or optionally substituted (C6-12)aralkyl;

R is a group selected from

---- is a single bond or double bond.

2. The compound of claim 1 wherein said compound has the Formula II:

Formula II or a stereoisomer, solvate and/or pharmaceutical acceptable salt thereof; wherein
A, $R_1$, $R_2$, $R_3$ and R, are as defined in claim 1.

3. The compound of claim 2, wherein $R_1$ is H, methyl or benzyl and $R_2$ is H or methyl.

4. The compound of formula (I) of claim 1 wherein substituents on optionally substituted aryl or optionally substituted (C6-12)aralkyl in $R_3$, $R_1$ and $R_2$ are selected from (C1-6)alkyl, (C1-6)alkoxy, halogen, halogen substituted (C1-6)alkyl, hydroxyl or amino.

5. A method of treating infectious disease caused by Venezuelan equine encephalitis virus (VEEV) comprising administering a compound to the patient, wherein the compound has the Formula (I):

Formula I or a stereoisomer, solvate and/or pharmaceutical acceptable salt thereof; wherein
A is $C(O)OR_3$ or $S(O_2)R_3$;
$R_3$ is (C1-6)alkyl, (C3-7) cycloalkyl, (C3-7)cycloalkyl(C1-5)alkyl, optionally substituted aryl, or optionally substituted (C6-12)aralkyl;
$R_1$ and $R_2$ are independently selected from H, (C1-6)alkyl, (C3-7)cycloalkyl, (C3-7)cycloalkyl(C1-5)alkyl, optionally substituted aryl, or optionally substituted (C6-12)aralkyl;
R is a group selected from ---- is a single bond or double bond.

6. A composition comprising a compound configured to act as an inhibitor of the cysteine protease domain of Venezuelan equine encephalitis virus (VEEV's) non-structural protein 2 (nsp2), wherein the compound has the Formula (III):

Formula III or a stereoisomer, solvate and/or pharmaceutical acceptable salt thereof; wherein
$R_4$ is (C1-6)alkyl, (C3-7)cycloalkyl, (C3-7)cycloalkyl(C1-5)alkyl, optionally substituted aryl, or optionally substituted (C6-12)aralkyl;
$R_5$ and $R_6$ are independently selected from H, (C1-6)alkyl, (C3-7)cycloalkyl, (C3-7)cycloalkyl(C1-5)alkyl, optionally substituted aryl, or optionally substituted (C6-12)aralkyl;

$R_7$ is a group selected from

[structures shown]

7. The composition of claim 6, wherein $R_5$ is H.

8. The composition of claim 6, wherein $R_5$ is $CH_3$.

9. The composition of claim 6, wherein $R_5$ is benzyl.

10. The composition of claim 6, wherein $R_6$ is H.

11. The composition of claim 6, wherein $R_6$ is $CH_3$.

12. The composition of claim 6 wherein substituents on optionally substituted aryl or optionally substituted (C6-12)aralkyl in $R_4$, $R_5$ and $R_6$ are selected from (C1-6)alkyl, (C1-6)alkoxy, halogen, halogen substituted (C1-6)alkyl, hydroxyl or amino.

13. The compound of claim 10, selected from:

[structures shown]

14. A method of treating infection by Venezuelan equine encephalitis virus (VEEV) comprising administering a compound to the patient, wherein the compound has the Formula (III):

[structure shown]

Formula III or a stereoisomer, solvate and/or pharmaceutical acceptable salt thereof; wherein $R_4$ is (C1-6)alkyl, (C3-7)cycloalkyl, (C3-7)cycloalkyl(C1-5)alkyl, optionally substituted aryl, or optionally substituted (C6-12)aralkyl;

$R_5$ and $R_6$ are independently selected from H, (C1-6)alkyl, (C3-7)cycloalkyl, (C3-7)cycloalkyl(C1-5)alkyl, optionally substituted aryl, or optionally substituted (C6-12)aralkyl;

$R_7$ is a group selected from

[structures shown]

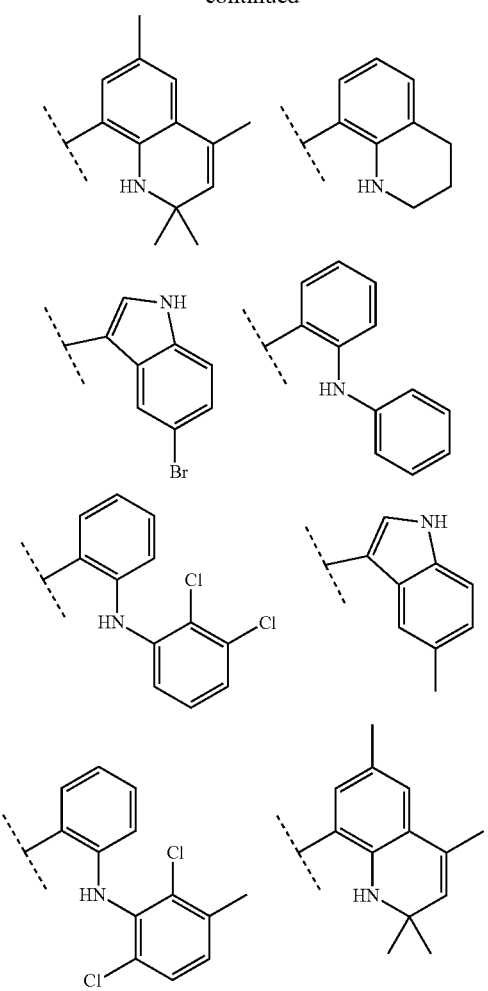
15. The composition of claim 1, wherein the compound is selected from:
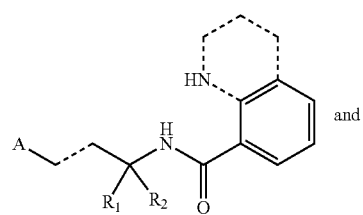
and
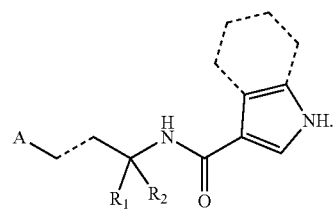
16. The composition of claim 1, wherein the compound is selected from:
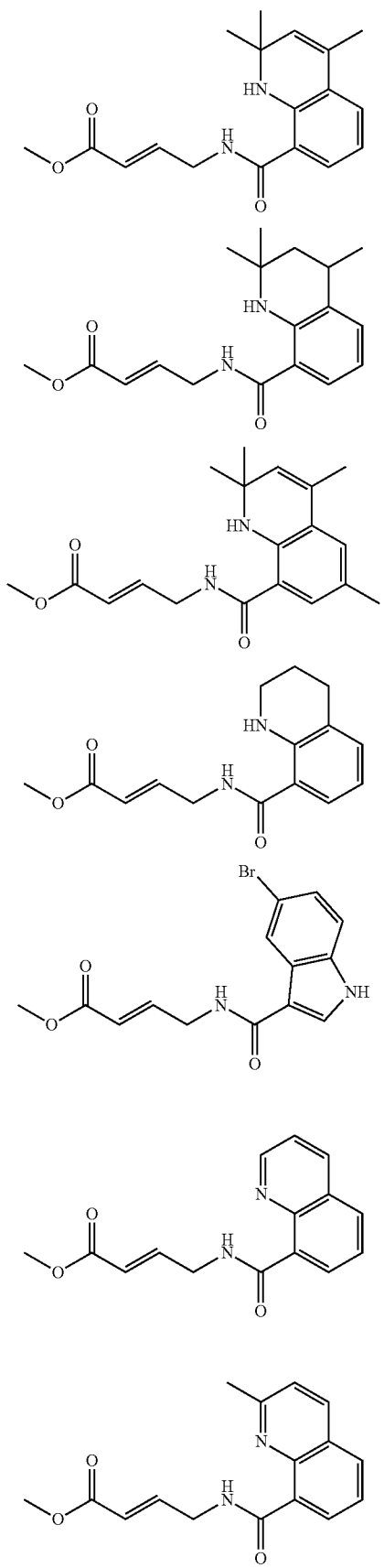

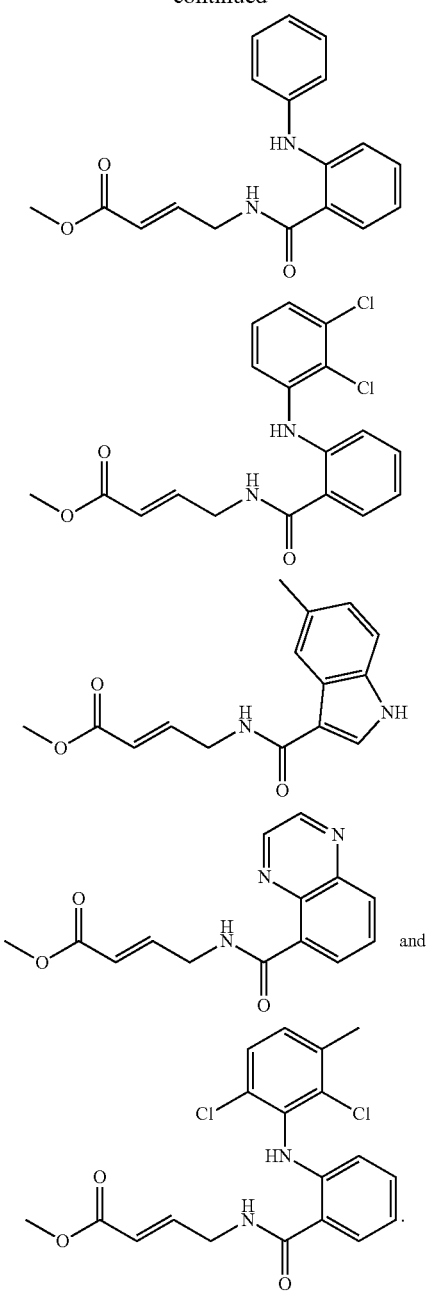
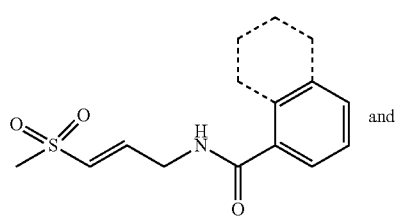
17. The composition of claim 6, wherein the compound is selected from:
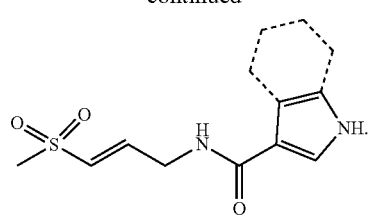
18. The composition of claim 6, wherein the compound is selected from:
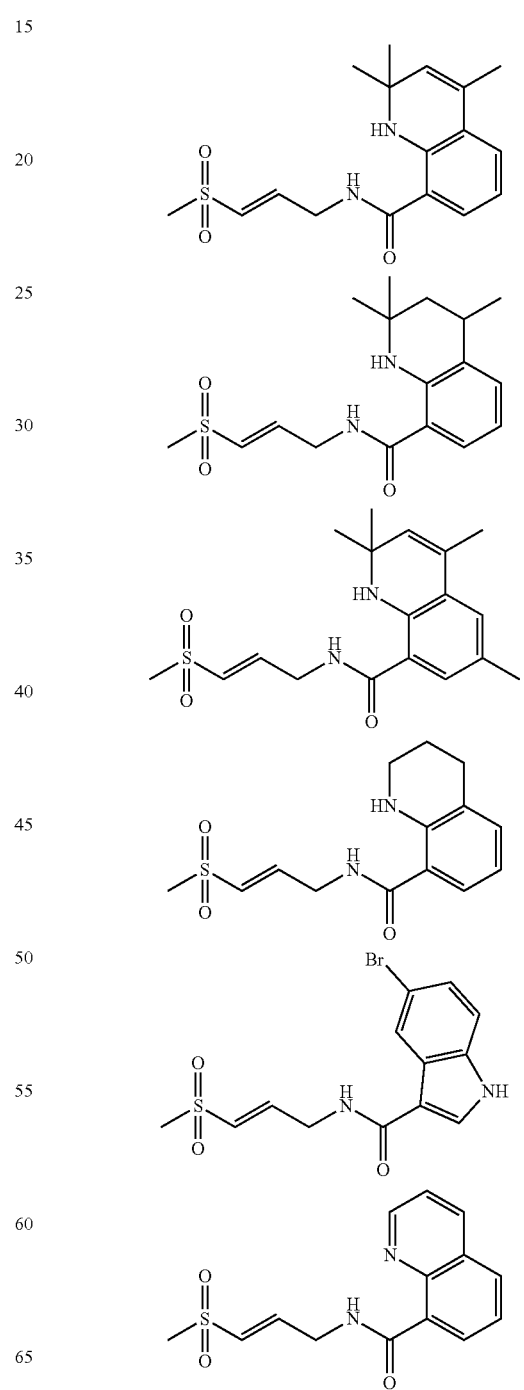

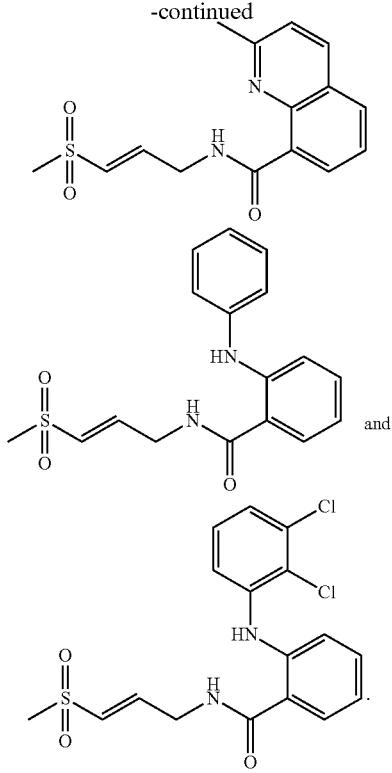
* * * * *